(12) United States Patent
Cha et al.

(10) Patent No.: US 10,978,176 B2
(45) Date of Patent: Apr. 13, 2021

(54) MACHINE LEARNING SYSTEMS AND METHODS FOR PREDICTING RISK OF RENAL FUNCTION DECLINE

(71) Applicant: pulseData Inc., New York, NY (US)

(72) Inventors: Theodore Cha, New York, NY (US);
Hai Po Sun, New York, NY (US);
Chris Kipers, New York, NY (US);
Oliver Fielding, New York, NY (US);
Jung Hoon Son, New York, NY (US);
Edward Lee, Astoria, NY (US)

(73) Assignee: pulseData Inc., New York, NY (US)

( * ) Notice: Subject to any disclaimer, the term of this patent is extended or adjusted under 35 U.S.C. 154(b) by 0 days.

(21) Appl. No.: 16/459,469

(22) Filed: Jul. 1, 2019

(65) Prior Publication Data

US 2020/0005900 A1   Jan. 2, 2020

Related U.S. Application Data

(60) Provisional application No. 62/692,450, filed on Jun. 29, 2018.

(51) Int. Cl.
| | |
|---|---|
| *G16B 40/00* | (2019.01) |
| *G16H 50/30* | (2018.01) |
| *G16B 50/00* | (2019.01) |
| *G16C 20/70* | (2019.01) |
| *G16H 10/40* | (2018.01) |
| *G16H 10/60* | (2018.01) |

(52) U.S. Cl.
CPC ............ *G16B 40/00* (2019.02); *G16B 50/00* (2019.02); *G16C 20/70* (2019.02); *G16H 10/40* (2018.01); *G16H 50/30* (2018.01); *G16H 10/60* (2018.01)

(58) Field of Classification Search
None
See application file for complete search history.

(56) References Cited

U.S. PATENT DOCUMENTS

| | | |
|---|---|---|
| 4,796,179 A | 1/1989 | Lehman et al. |
| 4,860,204 A | 8/1989 | Gendron et al. |
| 5,210,837 A | 5/1993 | Wiecek |
| 5,481,741 A | 1/1996 | McKaskle et al. |
| 5,612,866 A | 3/1997 | Savanyo et al. |
| 5,732,277 A | 3/1998 | Kodosky et al. |
| 5,966,072 A | 10/1999 | Stanfill et al. |
| 6,219,628 B1 | 4/2001 | Kodosky et al. |
| 6,272,672 B1 | 8/2001 | Conway |
| 7,164,422 B1 | 1/2007 | Wholey et al. |
| 7,167,850 B2 | 1/2007 | Stanfill |
| 7,506,304 B2 | 3/2009 | Morrow et al. |
| 7,716,630 B2 | 5/2010 | Wholey et al. |
| 7,720,779 B1 | 5/2010 | Perry et al. |
| 7,769,982 B2 | 8/2010 | Yehia et al. |
| 8,667,381 B1 | 3/2014 | Feng et al. |
| 8,694,947 B1 | 4/2014 | Venkataramani et al. |
| 9,003,360 B1 | 4/2015 | Feng et al. |
| 9,575,736 B2 | 2/2017 | Hong et al. |
| 9,971,570 B2 | 5/2018 | Sevenich et al. |
| 10,025,566 B1 | 7/2018 | Ahmed et al. |
| 2001/0020291 A1 | 9/2001 | Kudukoli et al. |
| 2001/0052110 A1 | 12/2001 | Orbanes et al. |
| 2002/0089538 A1 | 7/2002 | Wenzel et al. |
| 2003/0046663 A1 | 3/2003 | Rogers et al. |
| 2003/0071842 A1 | 4/2003 | King et al. |
| 2003/0132964 A1 | 7/2003 | Santori et al. |
| 2004/0107414 A1 | 6/2004 | Bronicki et al. |
| 2005/0257194 A1 | 11/2005 | Morrow et al. |
| 2007/0203683 A1 | 8/2007 | Kornerup et al. |
| 2007/0271381 A1 | 11/2007 | Wholey et al. |
| 2008/0049022 A1 | 2/2008 | Sherb et al. |
| 2008/0120296 A1 | 5/2008 | Kariathungal et al. |
| 2008/0270185 A1 | 10/2008 | Gossler et al. |
| 2010/0153910 A1 | 6/2010 | Ciolfi et al. |
| 2011/0078652 A1 | 3/2011 | Mani et al. |
| 2012/0077690 A1 | 3/2012 | Singbartl et al. |
| 2013/0346647 A1 | 12/2013 | Carrick et al. |
| 2014/0095943 A1 | 4/2014 | Kohlenberg et al. |
| 2014/0257852 A1 | 9/2014 | Walker et al. |
| 2016/0015701 A1 | 1/2016 | Zager et al. |
| 2016/0062749 A1 | 3/2016 | Stanfill et al. |
| 2017/0115310 A1 | 4/2017 | Colhoun et al. |

(Continued)

OTHER PUBLICATIONS

Charleonnan, Anusorn et. al., Predictive Analytics for Chronic Kidney Disease Using Machine Learning Techniques, 2016 Management and Innovation Technology International Conference (MITicon), 2016, pp. MIT-80-MIT-83, Bang-Saen, Chonburi, Thailand.

Coca, Steven G. et al., Plasma Biomarkers and Kidney Function Decline in Early and Established Diabetic Kidney Disease, J. Am. Soc. Nephrol., Sep. 2017, pp. 2786-2793, 28(9), American Society of Nephrology.

Faddoul, Geovani et al., Analysis of biomarkers within the initial 2 years posttransplant and 5-year kidney transplant outcomes: results from Clinical Trials in Organ Transplantation-17, Transplantation, Apr. 2018, pp. 673-680, 102(4), CTOT-17 consortium.

(Continued)

*Primary Examiner* — Lori A. Clow
(74) *Attorney, Agent, or Firm* — Zeller IP Group PLLC; Kyle M. Zeller

(57) ABSTRACT

Systems, methods and apparatuses are described herein that employ machine learning techniques to assess a likelihood or risk that one or more patients will experience an adverse outcome, such as a decline in renal function, within one or more timeframes. The embodiments may utilize patient data relating to demographics, vital signs, diagnoses, procedures, diagnostic tests, biomarker assays, genetic tests, behaviors, and/or patient symptoms, to determine risk information, such as important predictive features and patient risk scores. And the embodiments may automatically execute patient workflows, such as providing treatment recommendations to providers and/or patients, based on determined risk scores.

19 Claims, 6 Drawing Sheets

(56) References Cited

U.S. PATENT DOCUMENTS

| | | |
|---|---|---|
| 2017/0337241 A1 | 11/2017 | Newbern et al. |
| 2017/0344672 A1 | 11/2017 | Gould et al. |
| 2018/0342324 A1 | 11/2018 | Cha et al. |
| 2019/0220975 A1 | 7/2019 | Hsieh et al. |

OTHER PUBLICATIONS

Huopaniemi, Ilkka et al., Disease progression subtype discovery from longitudinal EMR data with a majority of missing values and unknown initial time points, AMIA Annual Symposium proceedings AMIA Symposium 2014, Nov. 14, 2014, pp. 709-718, 2014, American Medical Informatics Association.

International Search Report and Written Opinion issued for PCT/US19/40200, dated Sep. 20, 2019, pp. 8.

Levey, Andrew S. et al., A New Equation to Estimate Glomerular Filtration Rate, Ann. Intern. Med., May 5, 2009, pp. 604-612, 150(9).

Mansour, Sherry et al., Biomarkers for the detection of renal fibrosis and prediction of renal outcomes: a systematic review, BMC Nephrology, Feb. 20, 2017, p. 72, 18(1), 13 pages.

Nadkarni, Girish N. et al., A Machine Learning Approach to Predicting End Stage Renal Disease, American Society of Nephrology, Nov. 4, 2017, Abstract: SA-OR057, 2 pages.

Nadkarni, Girish N. et al., Big data in nephrology: promises and pitfalls, Kidney Int., Aug. 2016, pp. 240-241, 90, International Society of Nephrology.

Nadkarni, Girish N. et al., Development and validation of an electronic phenotyping algorithm for chronic kidney disease, AMIA Annu. Symp. Proc., Nov. 14, 2014, pp. 907-916, 2014.

Nadkarni, Girish N. et al., Plasma biomarkers are associated with renal outcomes in individuals with APOLI1 risk variants, Kidney Int., Apr. 20, 2018, pp. 1409-1416, 2018:93(6).

Razavian, Narges et al., Multi-task Prediction of Disease Onsets from Longitudinal Lab Tests, Machine Learning for Healthcare Conference, Sep. 20, 2016, pp. 73-100.

Razavian, Narges et al., Temporal Convolutional Neural Networks for Diagnosis from Lab Tests, arXiv preprint arXiv:1511.07938v4, Mar. 11, 2016, 19 pages.

Singh, Anima et al., Incorporating temporal EHR data in predictive models for risk stratification of renal function deterioration, J. Biomed. Inform., Feb. 2015, pp. 220-228, 53.

Tangri, Navdeep et al., A Dynamic Predictive Model for Progression of CKD, Am. J. Kidney Dis., Apr. 2017, pp. 514-520, 69(4).

Tangri, Navdeep et al., A predictive model for progression of chronic kidney disease to kidney failure, JAMA., Apr. 20, 2011, pp. 1553-1559, 305(15).

Tangri, Navdeep et al., Multinational Assessment of Accuracy of Equations for Predicting Risk of Kidney Failure: a Meta-analysis, JAMA., Jan. 12, 2016, pp. 164-174, 315(2), Chronic Kidney Disease Prognosis Consortium Data Coordinating Center.

Tangri, Navdeep et al., Pro: Risk scores for chronic kidney disease progression are robust, powerful and ready for implementation, Nephrol. Dial. Transplant., May 1, 2017, pp. 748-751, 32(5).

Tummalapalli, Lekha et al., Biomarkers for predicting outcomes in chronic kidney disease, Curr. Opin. Nephrol. Hlypertens., Nov. 2016, pp. 480-486, 25(6), Wolters Kluwer Health, Inc.

Udler, Miriam S. et al., Effect of Genetic African Ancestry on eGFR and Kidney Disease, J. Am. Soc. Nephrol., Jul. 2015, pp. 1682-1692, 26(7), American Society of Nephrology.

MACHINE LEARNING SYSTEMS AND METHODS FOR PREDICTING RISK OF RENAL FUNCTION DECLINE

CROSS-REFERENCE TO RELATED APPLICATIONS

The present application claims benefit of U.S. provisional patent application Ser. No. 62/692,450, titled "Machine Learning Systems and Methods for Determining Risk of End Stage Renal Disease from Patient Information," filed Jun. 29, 2018, which is incorporated by reference herein in its entirety.

BACKGROUND

This specification relates to applications, systems and methods that employ machine learning models to predict risk of patient outcomes, such as renal function decline, from electronic patient data.

Predictive analytics is an emerging approach for disease treatment and prevention that uses data and statistical algorithms to identify the likelihood of future outcomes based on historical data. In healthcare applications, a primary goal of predictive analytics is to develop quantitative models that can be used to determine a patient's current health status and to predict specific future events or developments. In particular, for disease treatment and prevention, predictive analytics may take into account individual variability in genes, environment, health, and lifestyle.

Recently, risk prediction of renal function decline and progression to end-stage renal disease ("ESRD") has become a research priority. Early diagnosis and initiation of disease management of chronic kidney disease ("CKD") may delay the need for emergency dialysis, transplantation or renal replacement therapy; slow the progression of CKD; and allow for identification of reversible and modifiable disease risk factors. Importantly, studies have demonstrated that timely nephrology visits have been associated with reduced mortality and hospitalization.

Existing tools that predict risk of renal function decline and progression to ESRD have received widespread attention and validation. In particular, the Kidney Failure Risk Equation ("KFRE") is seen as the current prevailing standard for ESRD risk prediction in North American patients with CKD Stages 3 to 5. The KFRE makes use of four clinical variables: age, sex, estimated glomerular filtration rate ("eGFR") and urine albumin-to-creatinine ratio ("UACR"); each variable is assigned a standard weight for a traditional risk score calculation. The KFRE is detailed in Navdeep Tangri et al., "Multinational Assessment of Accuracy of Equations for Predicting Risk of Kidney Failure: A Meta-analysis," JAMA, 315:2 (2016) pp. 164-174, which is incorporated by reference herein in its entirety.

While the KFRE offers mathematically significant predictive models for ESRD prediction, it falls short in clinical practice. First, the KFRE's reliance on eGFR and UACR significantly limits the population on which risk scores can be calculated; most patients for whom such information is available have already received a nephrology consult. Accordingly, the KFRE often proves to be an impractical way of assessing risk across a population in order to identify those at highest risk of unplanned dialysis starts. Moreover, because the KFRE presents a fixed score based on one-time values, it does not take into account the natural longitudinal variability of laboratory results.

Accordingly, there is a need for improved predictive modeling systems and methods that could aid clinicians in their assessment of the risk of renal function decline and/or progression to ESRD. It would be beneficial if such systems and methods allowed for risk-stratification across patient populations to drive preemptive care. It would be further beneficial if such systems and methods could leverage the widespread use of electronic health records ("EHR") systems in order to identify important risk factors and utilize such information to accurately predict risk of renal function decline and/or progression to ESRD.

SUMMARY

In accordance with the foregoing objectives and others, exemplary computer-implemented methods, apparatuses, systems, and computer-readable media are disclosed herein that employ machine learning techniques to assess a likelihood or risk that one or more patients will experience an adverse outcome, such as a decline in renal function. The disclosed embodiments may utilize electronic patient data received from any number of data sources to determine such risk information. For example, the embodiments may employ data relating to patient demographics, vital signs, diagnoses, procedures, various diagnostic tests (e.g., blood serum, blood plasma, and/or urine tests), biomarker assays, genetic tests, behaviors, signs symptoms, and/or others.

The embodiments may also provide functionality to help organizations understand risk factors that lead to adverse renal outcomes and to determine which patients are at an increased risk of experiencing such outcomes within various timeframes. For example, the embodiments may determine various features from electronic patient data, analyze such features via one or more machine learning models to determine predictive features for a particular outcome, and/or determine the likelihood that particular patients will experience the outcome within one or more timeframes (e.g., via calculation of risk scores).

The disclosed embodiments may be configured to transmit or display risk information, such as important risk factors, weights associated with such risk factors, and/or patient risk scores, to users via one or more client applications or application programming interfaces ("APIs"). In certain cases, the embodiments may utilize determined risk information to automatically execute patient workflows, such as notifying various providers when a patient requires additional medical care, scheduling patient appointments, and/or providing treatment recommendations and educational materials.

In one embodiment, a computer-implemented method is provided to determine a risk of renal function decline for a patient. The method may include analyzing, by a computer, input data received from one or more data sources to determine patient information associated with a patient. The patient information may include one or more demographics associated with the patient and each demographic may be associated with demographic information, such as but not limited to, demographic identifier and a demographic value. Exemplary demographics may relate to an age of the patient, a gender of the patient and/or a race of the patient.

The patient information may also include one or more lab tests associated with the patient. Each of the lab tests may be associated with lab test information, for example, a lab test variable and a lab test value relating to the variable. In certain cases, the lab test information may additionally or alternatively include a lab test identifier, a lab test date, a unit relating to the lab test value, a reference range of values, a sample type, facility identification information, provider information, radiological imaging data, and/or clinical notes. Exemplary lab tests may include those associated with a lab test variable selected from tumor necrosis factor receptor-1 ("TNFR1"), tumor necrosis factor receptor-2 ("TNFR2") and/or kidney injury molecule-1 ("KIM1"). In one embodiment, the lab tests may include at least one lab test associated with TNFR1, at least one lab test associated with TNFR2 and at least one lab test associated with KIM1. Moreover, the lab tests may further include one or more lab tests associated with one or more of the following lab test variables: estimated glomerular filtration rate ("eGFR"), urine albumin-creatinine-ratio ("UACR"), serum creatinine, blood urea nitrogen ("BUN"), serum sodium, serum potassium, serum chloride, serum bicarbonate, serum calcium, serum albumin, urine creatinine, urine albumin, urine microalbumin, urine protein, complete blood count ("CBC"), liver function, lipid profile, a coagulation panel, magnesium, phosphorus, brain natriuretic peptide ("BNP"), hemoglobin A1c ("HbA1c"), uric acid and/or endostatin.

The method may further include calculating, by the computer, an initial value for each of a plurality of features, based on the patient information. The features may include, for example, a plurality of demographic features, such that each demographic feature relates to at least one demographic of the one or more demographics included in the patient information. The features may further include a plurality of lab test features, such that each lab test feature relates to at least one lab test of the one or more lab tests included in the patient information.

The method may also include applying, by the computer, a feature-specific weight to the initial value of each of the plurality of features to thereby determine a final value for each of the plurality of features; calculating, by the computer, a risk score for the patient, based on the final values of the features, the risk score relating to a probability that the first patient will experience an outcome relating to a decline in renal function within a predetermined amount of time; and/or outputting the risk score. In certain embodiments, the method may optionally include determining that the risk score satisfies a workflow rule associated with a patient workflow; and executing the patient workflow, based on said determining that the risk score satisfies said workflow rule. A patient workflow may include, for example, determining a treatment recommendation for the patient, based on the risk score and transmitting a notification comprising the treatment recommendation to one or more recipients.

In some cases, the patient information may include one or more diagnoses associated with the patient. Each of the diagnosis may be associated with diagnosis information, such as but not limited to: a diagnosis identifier, a diagnosis date, provider information, equipment information, clinical notes and/or vital signs information. Exemplary diagnoses may relate to kidney issues, such as polycystic kidney disease, renal agenesis, Alport Syndrome, rapidly progressive glomerulonephritis, focal segmental glomerulosclerosis, IgA nephropathy, membranous nephropathy, membranoproliferative glomerulopathy, mesangial proliferative glomerulopathy, minimal change disease, nephritis syndrome, nephrotic syndrome, nephrolithiasis, hypertensive nephropathy, analgesic nephropathy, diabetic nephropathy, lithium nephropathy, renal artery stenosis, Lupus nephritis, kidney myeloma, kidney amyloidosis, anti-glomerular basement disease, fatigue or weakness, edema, and proteinuria. Other exemplary diagnoses may relate to comorbidities, such as but not limited to: alcohol abuse, anemia deficiency, rheumatoid arthritis, blood loss anemia, cardiac arrhythmia, congestive heart failure ("CHF"), chronic pulmonary disease ("CPD"), coagulopathy, acquired immunodeficiency syndrome ("AIDS") or human immunodeficiency virus ("HIV"), depression, diabetes, drug abuse, hypertension, hypothyroidism, liver disease, lymphoma, a fluid or electrolyte disorder, metastatic cancer, a neurological disorder, obesity, paralysis, peripheral vascular disease, psychosis, and pulmonary circulation disorder. When the patient information includes diagnoses, the plurality of features may also include a plurality of diagnosis features. For example, each diagnosis feature may relate to at least one diagnosis of the one or more diagnoses.

Additionally or alternatively, the patient information may include one or more medications associated with the patient. Each of the medications may be associated with medication information, such as but not limited to: a medication identifier, a medication date, a medication type, a concentration, a quantity, an amount, date information, refill information, provider information, and/or clinical notes. The medications may include, for example, any of the following: antibiotics, non-steroidal anti-inflammatory drugs ("NSAID"), beta-adrenergic receptor blockers, a dihydropyridine medications, angiotensin II receptor blockers ("ARBs"), angiotensin-converting enzyme ("ACE") inhibitors, sodium-glucose Cotransporter-2 (SGLT2) inhibitors, Thiazide-class diuretics, Loop-diuretics and/or HMG-CoA reductase inhibitors. When the patient information includes medications, the plurality of features may also include a plurality of medication features, where each medication feature relates to at least one medication.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

Figure 1:
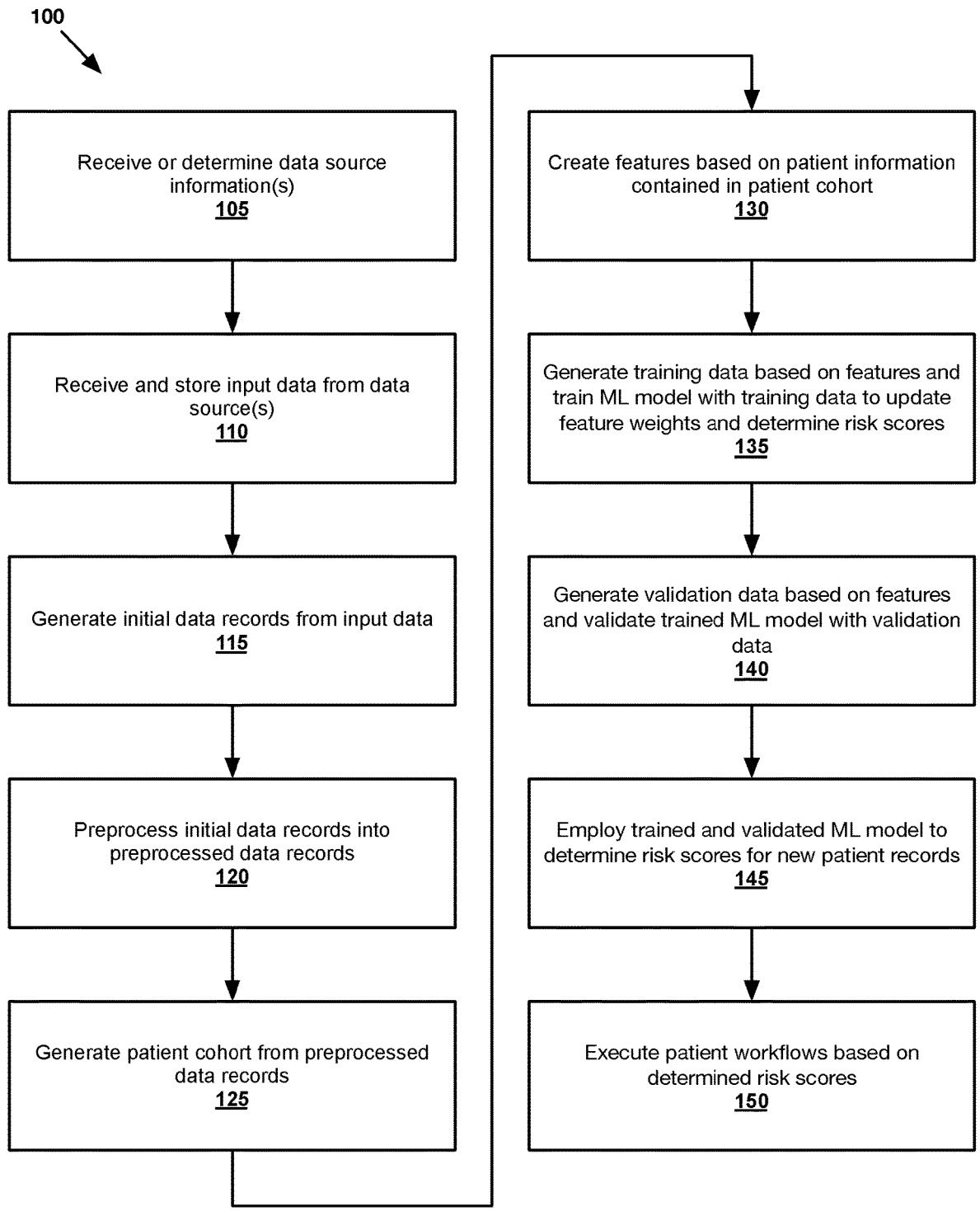
FIG. 1 shows an exemplary method 100 of determining risk information for any number of patients in accordance with one or more embodiments presented herein.

Various data processing platforms embodied in systems, computer-implemented methods, apparatuses and/or software applications are described herein to predict risk of adverse patient outcomes, such as renal function decline, for any number of patients. By utilizing various informatics, phenotyping, and data standardization techniques, the embodiments allow electronic patient data, such as longitudinal EHRs, biomarker assays and/or genomics data, derived from any number of data sources to be leveraged for improved care delivery.

The embodiments may employ machine learning models to determine predictive features for a given patient outcome from electronic patient data and/or to determine the importance of such features. The embodiments may evaluate such features for any number of patients to determine the likelihood that each patient will experience the outcome within one or more timeframes (e.g., via calculation of risk scores).

The embodiments may also be adapted to execute one or more patient workflows based on determined risk scores. For example, when the patient's risk score is within a certain range or is greater than a certain threshold, the embodiments may transmit various alerts or notifications to a patient and/or to any number of providers associated with the patient. Such notifications may include relevant patient information, important risk information, and/or one or more treatment recommendations determined by the system.

It will be appreciated that the term "machine learning" generally refers to algorithms that give a computer the ability to learn without being explicitly programmed, including algorithms that learn from and make predictions about data. Machine learning algorithms employed by the embodiments disclosed herein may include, but are not limited to, random forest ("RF"), least absolute shrinkage and selection operator ("LASSO") logistic regression, regularized logistic regression, XGBoost, decision tree learning, artificial neural networks ("ANN"), deep neural networks ("DNN"), support vector machines, rule-based machine learning, and/or others.

For clarity, algorithms such as linear regression or logistic regression can be used as part of a machine learning process. However, it will be understood that using linear regression or another algorithm as part of a machine learning process is distinct from performing a statistical analysis such as regression with a spreadsheet program. Whereas statistical modeling relies on finding relationships between variables (e.g., mathematical equations) to predict an outcome, a machine learning process may continually update model parameters and adjust a classifier as new data becomes available, without relying on explicit or rules-based programming.

The disclosed machine learning embodiments are typically employed to determine risk information for patient outcomes that relate to renal function. In cases where an outcome relates to a level of renal function (e.g., a decline to a certain level and/or a percentage decline from a baseline level), eGFR may generally be utilized to represent such level at any given time.

eGFR is a mathematically derived entity based on a patient's serum creatinine level. A number of well-validated equations may be employed to calculate eGFR, including the MDRD and CKD-EPI equations. In certain embodiments, the system may calculate eGFR values from a patient's recorded serum creatinine results and/or may recalculate eGFR values found in patient records according to the CKD-EPI equation:

$$eGFR = 141 * \min(Scr/\kappa, 1)\alpha * \max(Scr/\kappa, 1) - 1.209 * 0.993^{Age} * 1.018[\text{if female}] * 1.159[\text{if black}]$$

where: Scr is serum creatinine (mg/dL); $\kappa$ is 0.7 for females and 0.9 for males; $\alpha$ is −0.329 for females and −0.411 for males; min indicates the minimum of Scr/$\kappa$ or 1; and max indicates the maximum of Scr/$\kappa$ or 1.

It will be appreciated that a patient's renal function may be determined based on a plurality of individual eGFR values occurring within a certain period of time. For example, a patient's renal function may be determined by averaging two or more eGFR values occurring over a period of from about 30 to about 180 days (e.g., 90 days).

In certain embodiments, the machine learning models may be employed to determine risk information for patient outcomes relating to a decline in renal function to a certain eGFR associated with a range of eGFR values. For example, a model may be employed to predict whether a patient's renal function will decline to an eGFR associated with a diagnosis or a group of diagnoses, such as CKD stage 3, CKD Stage 3a ("CKD3a"), CKD stage 3b ("CKD3b"), CKD stage 4, renal failure and/or others.

A CKD stage 3 diagnosis is associated with an eGFR of from 30 to less than 60 ml/min/1.73 m2. CKD3a and CKD3b diagnoses are subsets of CKD stage 3 and are associated with eGFR values of from 45 to less than 60 ml/min/1.73 m$^2$, and from 30 to less than 45 ml/min/1.73 m$^2$, respectively. And a CKD stage 4 diagnosis is associated with an eGFR value of from 15 to less than 30 ml/min/1.73 m$^2$.

Renal failure may be characterized by one or more of the following: a diagnosis of CKD stage 5, a diagnosis of ESRD, initiation of dialysis, a kidney transplant and an eGFR value of less than 15 ml/min/1.73 m$^2$. The term "RRT-required" is used herein to indicate renal failure that is characterized by an eGFR value of 10 ml/min/1.73 m$^2$ or less (rather than less than 15 ml/min/1.73 m$^2$).

Overview

Referring to FIG. 1, an exemplary method 100 of determining risk of a renal-related outcome for any number of patients is illustrated. As shown, the method begins at step 105, where the system receives and/or determines data source information corresponding to one or more data sources.

In one embodiment, the system may receive data source information from an application. For example, a user may manually enter data source information into a client application and/or may upload a file containing such information. In another embodiment, the system may be configured to automatically discover one or more data sources, along with any corresponding data source information. Exemplary data source information may comprise, for example, a name, location, type and/or access information of the data source.

Generally, the system may connect to any number of data sources that store patient information for one or more patients. Such data sources may include, but are not limited to: EHR systems (e.g., EPIC, CERNER, ALLSCRIPTS); health facility systems (e.g., systems associated with doctors' offices, laboratories, hospitals, pharmacies, etc.); insurance systems and claims databases; payment and billing systems; user devices (e.g., patient devices, provider devices, and/or administrator devices); medical and biometric devices; and/or various engagement systems (e.g., survey systems that store patient and/or provider survey responses). Other exemplary data sources may include, contact management systems, customer relationship management systems, scheduling systems, patient engagement systems, human resources systems, and/or cloud-based storage and backup systems.

Exemplary patient information stored by such data sources may comprise identification information, demographics information, diagnoses and procedures information ("DP information"), lab tests information, medications information, genetics information, and/or various information relating patient signs, symptoms and behaviors. In certain embodiments, such patient information may additionally or alternatively comprise medical device information (e.g., waveform data, biometrics, etc.), financial information, insurance information, claims information, and/or various patient-generated data (e.g., automated call responses, health risk assessment responses, patient surveys, etc.).

Patient identification information may comprise a unique ID, name, contact information (e.g., residence, mailing address, business address, email address, telephone number), emergency contact, national identification number, social security number, passport number, driver's license number, and/or facial images or features.

Demographics information comprises information relating to a patient's gender, ethnicity, race, age (e.g., birth date, birth year, age at a certain date), blood type, marital status, education, profession or occupation, employer information, income level and/or others.

DP information comprises information relating to patient admissions, discharges, transfers, appointments, inpatient events, outpatient events, and/or other medical encounters. Exemplary DP information may include, but is not limited to: one or more diagnosis and procedure codes ("DP codes"), date/time information (e.g., start date/time, end date/time, etc.), care information (e.g., type of care provided, medical procedure employed, etc.), equipment information, medical identification information, provider information, presence on admission, clinical notes, vital signs information, and/or others.

Lab tests information comprises information relating to one or more analyzed samples (e.g., biological fluids and excretions) isolated from any given patient. Exemplary lab tests information may include, but is not limited to: one or more lab test codes, test type, variable measured, a value or level of the measured variable, results, units, reference ranges, date/time information (e.g., test ordered date/time, test reported date/time), sample type (e.g., blood, blood serum, blood plasma, urine, saliva, sweat, tears, cerebrospinal fluid, biopsy, ascites, milk, lymph, bronchial and other lavage samples, or tissue extract), radiological imaging data, facility identification information, provider information, clinical notes and/or others.

Medications information comprises information relating to one or more medications administered or prescribed to a patient. Exemplary medications information may include, but is not limited to: one or more medication codes, medication name, medication type, concentration, quantity or amount, date/time information (e.g., start date/time, end date/time, date/time medication was administered, etc.), refill information, facility identification information, provider information, instructions or other clinical notes, and/or others.

Genetics information comprises information relating to the presence or absence of one or more risk variant alleles expressed by a patient. In one embodiment, genetics information may be provided in the form of one or more DNA-sequencing or molecular diagnostics tests results.

In certain embodiments, one or more data sources may comprise patient information relating to a patient's signs, symptoms and/or behaviors. Signs typically comprise objective findings (e.g., described by a provider) and such information is occasionally available in structured formats (e.g., abdominal tenderness, ICD-10 code R10.819). Symptoms may comprise the patient's subjective description of their condition or illness (e.g., "stomach pain") and such information is typically available in the form of unstructured clinical notes. Behaviors may comprise structured and unstructured information relating to patient characteristics, such as smoking status and/or illicit drug use.

As shown in FIG. 1, the system connects to the one or more data sources in order to ingest and store input data contained therein 110. In one embodiment, the system may run scheduled queries or processes to pull raw patient data from the data sources. In other embodiments, the system may provide an endpoint for authorized users to upload input data for processing.

At step 115, the system processes the ingested input data in accordance with a centralized data schema to create initial data records. In one embodiment, the system may determine various metadata relating to the input data and transactions associated therewith (e.g., an authorized user, a time of ingestion, data source information, row counts, patient counts, range of dates included in the data and/or others). The system may then associate such metadata with a corresponding initial data record.

At step 120, the system performs various preprocessing steps to clean, validate and/or normalize the initial data records into preprocessed data records. Such preprocessing may be required to create preprocessed data records comprising data tables having a standardized format or schema. As used herein, the term "table" is used in its broadest sense to refer to a grouping of data into a format providing for ease of interpretation or presentation. Such formats may include, but are not limited to, data provided from execution of computer program instructions or a software application, a table, a spreadsheet, etc.

EHR data is notoriously messy; it is often stored in multiple tables and can be very inconsistent. For example, diagnoses and procedures codes may be entered for billing purposes and such codes may not reflect an accurate or complete health record for a given patient. As another example, laboratory test results for a single patient may be stored in various formats across a plurality of laboratory-specific databases and may suffer from inconsistent labelling and use a plethora of different unit types. Although machine learning techniques are well-equipped to handle common problems of incomplete and/or inaccurate data, a significant amount of preprocessing, cleaning and/or regularization may be employed to ensure the creation of high-quality predictive features.

During preprocessing, the system may perform any number of data manipulations on the initial data records to create preprocessed data records therefrom. Some exemplary manipulations may include: joins (an operation performed to establish a connection between two or more database tables, thereby creating a relationship between the tables), filters (a program or section of code that is designed to examine each input or output request for certain qualifying criteria and then process or forward it accordingly), aggregations (a process in which information is gathered and expressed in a summary form for purposes such as statistical analysis), caching (i.e., storing results for later use), counting, renaming, searching, sorting, and/or other table operations. In one particular embodiment, the system may correlate or index the various ingested raw input data to corresponding unique patient records.

It will be appreciated that, although the initial data records may be stored in a different format than the original input data, these records will still contain any underlying patient information found in the input data. Accordingly, the system may perform various preprocessing steps to allow such information to be included in preprocessed data records. Such preprocessing ensures, for example, that all patient information associated with the preprocessed data records comprises standardized naming conventions, filesystem layout, and configuration variables.

In one embodiment, the system may identify demographics information from patient- and/or provider-generated input data, such as EHRs, automated call responses, health risk assessment responses, patient surveys, socio-economic surveys and others. Upon identifying such information in an initial data record, the system may aggregate, encode and sort this information into a combined, unique preprocessed data record for each patient.

The system may determine DP information based on DP codes identified within the input data records. Such DP codes may include any of the various International Classification of Diseases ("ICD") codes (e.g., ICDA-8, ICD-9, ICD-9-CM, ICD-O (Oncology), ICD-10 and ICD-10-CA (Canadian Enhancements), ICD-9-PCS, and ICD10-PCS), any Clinical Classification Software ("CCS") codes and/or others.

The system may also identify and group lab tests information into a manageable number of clinically meaningful categories (i.e., lab test groups) during preprocessing. In one embodiment, the system may map individual lab test names and/or codes found in an input data record to a corresponding Logical Observation Identifiers Names and Codes ("LOINC") code. A database of LOINC codes is maintained by Regenstrief Institute, Inc.

In another embodiment, the system may map individual lab test codes to one of a plurality of custom lab test groups, wherein each group corresponds to a clinically meaningful concept. For example, values associated with LOINC codes 27298-9 (Protein [Units/volume] in Urine) and 2887-8 (Protein [Presence] in Urine) can be preprocessed into quantitative values and included within preprocessed data records.

The system may perform any number of additional preprocessing steps to normalize lab tests information contained in the initial data records. In cases where lab test variable values comprise absolute values or concentrations expressed in different units, the system may convert the values to a singular, standardized unit. In other cases where such values comprise units relating to the output from an assay (e.g., a value indicative of the amount of a label for a variable, or the size of a peak from a chromatograph), the system may record continuous data as structured, standardized values (e.g., by recording the peak or nadir over a particular time period). And in yet other cases where values are provided in relation to another component of a sample in which the value was determined (e.g., a ratio of a first value of a first variable to a second value of a second variable), the system may store the ratio values within the preprocessed data.

In one embodiment, the system may determine medications information by identifying medication-related codes included in the input data records, such as the National Drug Code ("NDC") directory codes and/or Anatomical Therapeutic Chemical ("ATC") drug classification system codes. The NDC directory is maintained by the U.S. Food & Drug Administration ("FDA") according to Section 510 of the Federal Food, Drug, and Cosmetic Act (21 U.S.C. § 360). And ATC classifications are available online from the World Health Organization ("WHO"), and are updated and published once a year by the WHO Collaborating Centre for Drug Statistics Methodology.

During preprocessing, the system may map the medication information found in the initial data records to NDC codes and to a corresponding ATC code. Additionally or alternatively, the system may associate each of the NDC codes with a medication name corresponding to an entry in a normalized naming system. For example, the name of each medication corresponding to an NDC code may be selected from the RxNORM database, which comprises a normalized naming system for generic and branded drugs maintained by the U.S. National Library of Medicine.

Finally, the system may identify and preprocess any patient information pertaining to signs, symptoms and behaviors stored in the initial data records. Preprocessing of such sub-disease and non-disease descriptors often requires custom normalizer data representations that combine multiple terminology standards. For example, ICD-10-CM code Z72.0 ("Tobacco use"), SNOMED-CT code 20077176002 ("Smoker (finding)"), and a text excerpt from clinical notes such as "Patient is an active smoker," are semantically equivalent, and thus may be assigned the same representation during the preprocessing step. Clinical text may be extracted and processed via the use of regular-expression-based techniques and/or natural language processing ("NLP") techniques.

At step 125, the system may generate a patient cohort comprising a subset of the preprocessed data records by, for example, filtering out any records that do not meet a cohorting criteria. Generally, cohorting criteria may relate to any information included in the preprocessed data records, such as various patient information. For example, cohorting criteria may relate to one or more of: demographic information (e.g., age, gender, race), DP information (e.g., presence of a specific DP code), laboratory tests information (e.g., presence of a value for a specific variable and/or specific values for a given test), genetics information (e.g., presence of a particular high-risk allele), medications information (e.g., usage of one or more particular medications), health program enrollment status, payer plan enrollment status, and/or other.

It will be appreciated that, in many cases, a particular renal function decline outcome may only be applicable to a small subset of the patients included within the preprocessed data records. Accordingly, a cohorting criteria may be employed to precisely define a cohort comprising a population of interest and such a cohort may be employed to train a model.

As an example, a simple enrollment-based cohort can be derived using the patient's eligibility or enrollment status for a certain program, which may be recorded in the EHR data. As another example, cohorting criteria may relate to whether a patient record includes at least one calculated laboratory value for eGFR less than 60 ml/min/1.73 $m^2$; this could be used to select a cohort of patients who experienced even a minor decline in kidney function and thus may have CKD. And as yet another example, a cohorting criteria may relate to whether a record includes DNA-sequencing or molecule diagnostic information confirming the presence of the APOL1 high-risk allele (discussed below).

At step 130, various predictive features are created from the preprocessed patient information associated with each patient in the cohort. As discussed below, such features may be provided to the machine learning model to determine various risk information, such as a predictive value (i.e., a feature weight) of each feature and a risk score for each of the patients.

Generally, each of the features employed by the embodiments will comprise an individual value relating to one or more specific aspects of the processed patient information generated at step 120. And each feature may be created via one or more processing steps performed in relation to the associated attribute value(s), such as: converting various codes to standard codes, encoding categorical variables, standardizing continuous variables, log-scaling count variables, bucketing variables, binning variables, and/or determining values (e.g., counts, maximums, minimums, means, medians, modes, standard deviations, etc.).

In certain embodiments, features may be created by (1) subjecting patient information to any number of combinations, aggregations, transformations, normalizations and/or imputations, and (2) calculating one or more summary statistics for the resulting data. Exemplary summary statistics may include, but are not limited to: count, first date, last date, most-recent value, minimum value, maximum value, mean value, median value, modal value, standard deviation, quartiles, and/or trend over time.

It will be appreciated that summary statistics may be calculated over various time periods within a given observation window, for example, over a 45-, 90-, 180-, or 365-day period preceding the prediction start date and/or over the entire observation window. And it will be appreciated that each individual summary statistic value determined for a given time period may be employed as an individual feature.

As an example, any number of features may be created by performing multiple aggregations with respect to values associated with a single variable (i.e., an aspect of patient information). One example of this approach is to determine a daily median of attribute values, then a weekly median of the daily medians, and then a monthly median of weekly medians. Another example of this approach is to determine a daily median of attribute values and then a monthly minimum attribute value. These aggregation techniques have been found to create powerful predictive features as they remove the potential for extreme values to affect the overall data signal and they take into account the overall health level of a patient within a given time window.

As another example, various features may be created by binning values relating to a patient information attribute into a time period to give a sense of trend over time. For example, values associated with a particular lab test that were measured within a certain amount of time of a prediction start date may be binned (e.g., lab tests associated with a date that is within 90 days of prediction start date; or lab tests associated with a date that is within 90 to 185 days before the prediction start date). It will be appreciated that multiple features may be created for a single attribute by binning values into multiple time periods and determining summary statistics relating to the bins (and/or relating to comparisons of binned information).

Features may also be created by calculating ratios of values, ratios of value aggregations and/or ratios of value aggregation standardizations over one or more time periods. Additionally, various features relating to comparisons of such information may be created. As a specific example, the system may employ a feature relating to a patient's ratio of standardized median serum creatinine to standardized median bicarbonate over a 90-day period preceding the prediction start date. As discussed below, the machine learning models described herein may be employed to determine important ratios and combinations of patient information to achieve a high predictive performance.

The features discussed herein may employ standardized attribute values. An exemplary standardization technique for binned patient information may comprise: (1) determining a mean of all values in a group of aggregated variables and, for each value (2) determining the standard deviation of the value, (3) subtracting the mean from the value to determine a deviation; and (4) dividing the deviation by the standard deviation to arrive at a standardized value. It will be appreciated that standardization generally allows for a better understanding of the relationship of a value to the overall patient population (e.g., to identify outliers).

Specific examples of features that relate to binned and standardized patient information may include: standardized median eGFR within a 90-day period preceding the prediction start date, standardized maximum hemoglobin within 90-185 days preceding the prediction start date; and/or difference between standardized mean albumin 0-185 days and 185-365 days before prediction start date.

In certain embodiments, imputation techniques may be employed to generate trend-based patient information features (e.g., when EHR data is incomplete). In one embodiment, a lack of certain values may be considered to be informative, and Boolean features may be determined from preprocessed data to indicate when values are being imputed. In one specific embodiment, a method of cross-sectional, median-value imputation for continuous variables may be employed.

Finally, it will be appreciated that features may be standardized or transformed in various ways depending on the modeling technique employed (e.g., to make the model more stable). For example, a logistic regression model may be sensitive to extreme values and it can be helpful to aggregate patient information attributes into buckets and incorporate attributes individually as a feature. However, a random forest model is partition-based and, therefore, less sensitive to extreme values within a longitudinal-data-based feature.

In any event, the system may create and employ features relating to various attributes of the preprocessed patient information, such as: demographics information, DP information, lab tests information, medications information, genetics information, and/or any information relating to signs, symptoms and behaviors. As an example, the system may employ features relating to demographic information, such as current age, gender or race of the patient.

In order to create features based on DP information, the system may first aggregate such information into a manageable number of groups, where each group represents a curated ontology of medical events and/or conditions. In such cases, the system may map individual ICD codes found within the input data (and all information associated therewith) to one of the groups. Additionally or alternatively, the system may first map each ICD code to a corresponding CCS code (e.g., level 1, level 2, level 3 and/or level 4) and then map the CSS codes to the groups.

In one embodiment, the system may aggregate DP information into one of a number of primary groups and employ features relating to such groups. Exemplary primary groups may include, but are not limited to: a group relating to systemic diseases affecting the kidneys, such as cystic and polycystic kidney issues; a group relating to primary kidney diseases, such as glomerulonephritis and kidney stones; a group relating to diagnostic testing, such as urine testing, ECGs and routine exams; acute kidney injury ("AKI") events, ischemic heart disease ("IHD"), and/or a group relating to early warning signs of CKD, such as polyneuropathy, edema, fatigue and weakness.

The system may also aggregate DP information into one of a number of comorbidity groups to be employed as features. Generally, such comorbidity groups may correspond to specific comorbidities included in the Elixhauser Comorbidity Index ("ECI"), which is described in detail in Elixhauser A., et al. "Comorbidity measures for use with administrative data," Med. Care 36:1 (1998) pp. 8-27, incorporated by reference herein in its entirety. For example, comorbidity groups relating to any of the following ECI comorbidities may be employed: diabetes (complicated and uncomplicated), congestive heart failure ("CHF"), peripheral vascular disorders, liver disease, hypertension (complicated and uncomplicated), obesity, metastatic cancer.

In certain cases, features relating to comorbidity groups may be created by weighing comorbidities within the context of a single event (i.e., a medical encounter) to ensure DP codes are not counted multiple times for the same event. For example, a patient having CHF may be seen by multiple doctors during a single hospital stay and any number of such doctors may record a DP code associated with the CHF comorbidity DP group. In such case, the system may determine a single CHF comorbidity encounter, rather than multiple instances of CHF comorbidities.

In one embodiment, the system may employ one or more features relating to a calculated comorbidity score. For example, a comorbidity score may be calculated for one or more of the comorbidity groups according to the Charlson Comorbidity Index ("CCI") scoring system. The CCI assigns points based on the presence of comorbidities as well as the age of a patient, where a higher score is considered to be a more complex patient. See Charlson, Mary E., et al. "A New Method of Classifying Prognostic Comorbidity in Longitudinal Studies: Development and Validation," Journal of Chronic Diseases 5:40 (1986) pp. 373-383, incorporated by reference herein in its entirety.

It will be appreciated that any number of features relating to the above-described groups may be created and employed by the machine learning models. Generally, it has been found that the creation of such groups provides enhanced interpretability of the various DP information found in the input data and allows for more efficient incorporation of such information into downstream operations.

The system may further employ any number of features relating to lab tests information (e.g., lab tests associated with kidney function). In one embodiment, such lab tests features may relate to one or more of the following: serum creatinine, blood urea nitrogen ("BUN"), sodium, potassium, chloride, bicarbonate, calcium and urine microalbumin. Other features employed by the system may relate to lab tests associated with: components of complete blood count ("CBC"), liver function tests ("LFTs"), lipid profile, coagulation tests, calcium, magnesium, phosphorus, brain natriuretic peptide ("BNP"), and/or uric acid.

In certain embodiments, the system may employ various features relating to ratios of the above lab test values. For example, various features relating to one or more of the following ratios may be calculated and employed to determine risk information: BUN/creatinine ratio; BUN/bicarbonate ratio; calcium/creatinine ratio; bicarbonate/creatinine ratio; albumin/creatinine ratio; phosphorus/calcium ratio; and/or phosphorus/creatinine ratio.

Due to the importance of eGFR in ascertaining renal function, various features relating to a patient's eGFR results may be calculated and employed. Exemplary eGFR features may include, but are not limited to: a most-recent eGFR value; a most-recent eGFR value before a qualifying eGFR value (e.g., an eGFR value less than a predetermined value, such as 60 ml/min/1.73 m$^2$); a trend line of eGFR values across one or more time periods during the observation period (e.g., a 90-, 180-, or 365-day period preceding the prediction start date, or the entire observation period); a change in eGFR value over such time periods and/or the rate of change in eGFR value across the time periods. In one embodiment, the system may calculate eGFR values from recorded serum creatinine results and/or recalculate available eGFR values according to the CKD-EPI.

The system may also employ various features relating to a patient's urine albumin-to-creatinine ratio ("UACR"). Generally, UACR may be extracted from the preprocessed patient information when such information includes LOINC code 14959-1 and/or the system may calculate UACR using laboratory test values for spot urine creatinine (LOINC code 2161-8) and spot urine microalbumin (LOINC code 14957-5), where both results were captured in the same 24-hour period. A UACR of greater than 30 mg/g (i.e., Albuminuria) is a known marker for CKD and, as discussed below, UACR values may be employed to calculate the KFRE.

In certain embodiments, the system may employ features relating to blood levels of one or more of the following biomarkers: tumor necrosis factor receptor-1 ("TNFR1"), tumor necrosis factor receptor-2 ("TNFR2"), kidney injury molecule-1 ("KIM1") and/or endostatin. As discussed in Example 4, below, employing such biomarker features may improve risk prognostication when added to other clinical markers (e.g., eGFR and albuminuria) in diabetic patients with both preserved and impaired renal function.

TNFR1 and TNFR2 are the soluble forms of the TNF receptor. Two types of soluble TNF receptors have been identified in human serum and urine that neutralize the biological activities of TNF-alpha and TNF-beta. These binding proteins represent truncated forms of the two types of high-affinity cell surface receptors for TNF (TNFR-p60 Type B and TNFR-p80 Type A). Soluble TNFR1 corresponds to TNFR-p60 Type B. Soluble TNFR2 corresponds to TNFR-p80 Type A. In the TNF superfamily nomenclature, TNFR1 and TNFR2 are referred to as TNFRSF1A and TNFRSF1B, respectively. These apparent soluble forms of the receptors appear to arise as a result of shedding of the extracellular domains of the membrane-bound receptors.

KIM1 is an immunoglobulin superfamily cell-surface protein expressed on the apical membrane of proximal tubule cells and is highly upregulated on the surface of damaged kidney epithelial cells. Urinary concentrations of KIM1 have been shown to rise in response to acute renal injury. Urinary KIM1 has been evaluated as a prognostic marker in diabetic kidney disease but has not been consistently found to be a strong independent predictor of progression.

Endostatin is a type XVIII collagen that is a well-known inhibitor of angiogenesis, although the precise mechanism by which endostatin works is not fully understood. Serum endostatin levels has been under investigation as a marker for several inflammatory diseases including rheumatoid arthritis, psoriasis, Crohn's disease, and also as a biomarker for development of cardiovascular disease.

The system may further employ any number of features relating to medications information. In creating such features, the system may group potentially nephrotoxic medications into drug categories (e.g., using the ATC classification system). Such medication groupings may include, for example: antibiotics, non-steroidal anti-inflammatory drugs ("NSAIDs"), beta-adrenergic receptor blockers, dihydropyridines, angiotensin II receptor blockers ("ARBs"), angiotensin-converting enzyme ("ACE") inhibitors, Thiazide-class diuretics, Loop-diuretics, and HMG-CoA reductase inhibitors. In one embodiment, the system may employ features relating to the total number of prescriptions across a particular medication group, for example, over one or more time periods (e.g., 6 months, 12 months, 18 months, 24 months, 30 months, 36 months, etc.).

In one embodiment, the system may employ one or more features relating to genetics information. Such features may relate to, for example, whether a patient has expressed risk variant alleles in the Apolipoprotein L1 gene ("APOL1"). Genetic admixture studies have demonstrated that two distinct alleles in the APOL1 gene on chromosome 22 confer substantially increased risk for a number of kidney diseases in African Americans, including focal segmental glomerulosclerosis, HIV-associated nephropathy, and hypertension-attributable kidney disease. And the APOL1 high-risk genotypes (i.e., two copies of the APOL1 renal risk variants: G1/G1, G2/G2, or G1/G2) have been shown to be associated with increased risk of renal function decline.

Finally, the system may employ features relating to information associated with a patient's signs, symptoms and/or behaviors associated with renal function decline. Exemplary features may relate to tobacco use, proteinuria, fatigue, edema and/or shortness of breath.

As shown in FIG. 1, the system may generate training data relating to some or all of the above features and employ the training data to train the machine learning model at step 135. In certain embodiments, each feature may be calculated from the patient information within an observation window and such information may be incorporated into a training data dataframe (e.g., as a column attached to a unique patient ID). The training data may then be provided to a machine learning model such that it may analyze the information contained therein to determine risk information.

Before a model can accurately determine risk information, it must be configured, trained and validated. In one embodiment, a user may input various model information into the system to configure a given machine learning model. Exemplary model information may include, but is not limited to, a definition of a target variable or outcome for which predictions are to be made (discussed below with respect to FIGS. 2-3), observation window information, prediction window information, transformation or activation functions information relating to the training data to be employed by the model and/or initial parameters/weights.

Exemplary observation window information may comprise an observation start date, an observation end date, and an observation period extending from the observation start date to the observation end date. Similarly, prediction window information may comprise a prediction start date, a prediction end date, and a prediction period extending from the prediction start date to the prediction end date. It will be appreciated that the observation window precedes the prediction window in time such that the observation end date occurs before the prediction start date.

Generally, the "learning" or "training" of a machine learning model refers to altering or changing model parameters to improve the overall predictive performance of the model. Determining the specific parameters w to be used in a model is an example of the more general problem of learning a mapping from data. Given a training data set D comprising a number N of examples of pairs of input and corresponding output observations (i.e., D={$(x_1,y_1)$}), the goal is to learn a mapping that approximates the mapping on the training set and, importantly, that also generalizes and/or extrapolates well to unseen test data drawn from the same probability distribution as the pairs in the training data set D.

To learn such a mapping, an error function is defined to measure the positive utility (in the case of an objective function) or the negative utility (in the case of a loss function) of a mapping that provides an output y' from input x when the desired output is y. When the error function is a loss function, the error on a given training dataset may be defined for a mapping as the sum of the losses (i.e., empirical loss).

Many error functions may be employed to train the disclosed machine learning models, including functions that include regularization terms that prevent overfitting to the training data, functions derived from likelihoods or posteriors of probabilistic models, functions that are based on sub-sampling large data sets, or other approximations to the loss function of interest (so called "surrogate loss functions"). Generally, the error may be computed either on the entire training data or may be approximated by computing the error on a small sub-sample (or mini-batch) of the training data.

Training generally occurs based on some example data D, by optimizing the error function E using an optimization algorithm. For example, the error function can be minimized by starting from some initial parameter values $w_0$ and then taking partial derivatives of E(w,D) with respect to the parameters w and adjusting w in the direction given by these derivatives (e.g., according to the steepest descent optimization algorithm). It will be appreciated that any number of optimization algorithms may be employed to train the disclosed machine learning models, including, for example, the use of stochastic gradients, variable adaptive step-sizes, $\eta\_t$, second-order derivatives, approximations thereof and/or combinations thereof.

In one embodiment, the machine learning models may be trained using elastic net logistic regression ("ENLR"), for example, with K-fold cross-validation, and random forest ("RF"). Both techniques mitigate over-fitting out-of-sample, while semi-automating feature selection given a set of potential features. ENLR facilitates feature selection and adds penalties to the logistic regression function for both LASSO and ridge regression penalties.

LASSO facilitates feature selection by shrinking parameters, while the ridge penalty penalizes for extreme parameter values and collinearity. The algorithm also addresses the unstable behavior of ordinary logistic regression where the number of examples is close to the number of features, therefore alleviating concerns when there is a need to evaluate a larger, richer, set of features. See, e.g., Zou, Hui et al., "Regularization and Variable Selection via the Elastic Net," J. R. Statist. Soc. B., 67:2 (2005) pp. 301-320; Tibshirani, Robert, "Regression Shrinkage and Selection via the Lasso," J. R. Statist. Soc. B., 58:1 (1996) pp. 267-288; and Tikhonov, A. N., "Solution of incorrectly formulated problems and the regularization method," Soviet Mathematics Doklady, 4 (1963) pp. 1035-1038 (each incorporated by reference herein in its entirety).

In certain embodiments, a K-fold (e.g., 10-fold) cross-validation technique (Monte Carlo-style) may be utilized. In such cases, the training dataset may be randomly partitioned into equal-sized sub samples in order to determine optimal penalty parameters for selecting predictive features that maximize the area under the curve ("AUC") of the receiver operating characteristics ("ROC") curve on the randomly selected samples across folds. LASSO and ridge weighting parameters may be established through grid evaluation, typically with a validation subsample of the training data. In certain embodiments where there are a relatively large number of categorical predictors, LASSO weighting parameters may be preferred.

As explained above, the high dimensionality of data available from EHR systems provides a large array of potential features for use in modeling. A common problem with general regression techniques is that using too many features can lead to the model overfitting on the training population, which leads to a decline in model performance and other instability issues (e.g., multicollinearity). A benefit of using machine learning techniques with built-in regularization is that such models automatically determine important, predictive features that will give the model the highest degree of success and robustness out-of-sample.

The RF approach mitigates overfitting by assembling many weak classifiers, or decision trees, to reduce out-of-sample variance. Such an approach implicitly handles interaction terms and nonlinearities. See Breiman, Leo, "Random forests," Machine Learning J. 45:1 (2001) pp. 5-32, incorporated by reference herein in its entirety. Two sources of randomness may be employed to reduce predictive variance: bagging (or batch aggregation) and feature bagging (or random variable selection). The batch aggregation technique behaves like built-in cross-validation that samples examples of the training set with replacement (while holding out the rest) in order to train many decision trees. The feature bagging technique is a built-in cross-validation that samples examples with replacement in order to train many trees; the method naturally handles interaction terms and nonlinearities, and tends to perform well "out-of-the box."

Generally, each calculated risk score may be employed to characterize, tag or otherwise classify patients into risk categories. The risk categories may represent quantitative stratifications or groupings of a patient population and/or patient cohorts, wherein each category is associated with an identifier, such as a relative risk percentage, a risk score range, a composite score or any numerical value that indicates the likelihood that a patient associated with the category will experience a particular outcome. In certain embodiments, the system may associate various qualitative descriptors with such risk categories (e.g., very low risk, low risk, medium risk, high risk, very high risk or combinations thereof). In one embodiment, the calculated risk score may be correlated to a monetary risk to an organization (e.g., a hospital).

At step 140, the model may be validated by repeating steps similar to 120-135 using one or more additional validation datasets. For example, the same or similar data preprocessing, feature calculation, and outcome calculation process can be repeated for one or more validation datasets. And the features can be fed into the trained ML model to score patients.

Performance metrics may also be calculated based on the patient scores and outcomes output by the model. It will be appreciated that a valid or robust model should expect similar performance metrics on the additional dataset as performance metrics calculated from a hold-out subsample of data that the model was originally trained on.

Generally, the above described training and validation process (or any subset thereof) may be repeated until a stopping criterion is reached. The stopping criterion may be any function that depends on the error or other performance measure computed on the training data, validation data or other data augmented to potentially include regularization term.

Once trained and validated, the machine learning models can determine risk information for new patient records as desired or required 145. Accordingly, newly available information may be re-ingested, preprocessed then features calculated for the ML model to calculate revised risk scores based on the relative feature weights generated on the training data. In one embodiment, the ML model may re-calculate the individual patient risk scores at regular intervals as new patient records are made available (e.g., daily, weekly or monthly). Moreover, the system may associate such risk scores with the corresponding patient record.

At step 150, the system may perform any number of additional actions, such as displaying information about one or more patient records and/or executing patient workflows based on the risk information associated with patient records.

In one embodiment, the system may transmit or display some or all information contained in one or more of the patient records (e.g., risk information and/or patient information) via one or more reports, notifications, alerts, webhooks, or API calls. For example, the system may transmit one or more of the patient records to a third-party system (e.g., EHR systems, lab systems, etc.). As another example, the patient records may be transmitted to, or otherwise accessed by, user devices associated with healthcare providers.

In another embodiment, the system may determine population information across a patient population or a subset thereof based on the patient records. In such cases, the system may store, output, transmit and/or display such population information. For example, the system may provide the population information to one or more users via one or more user interface screens of a client application, an API, and/or via creation of digital reports that may be stored, printed and/or displayed.

The system may be configured to execute various patient workflows designed to drive preemptive care and improve patient outcomes. In certain embodiments, the system may automatically select and execute a patient workflow upon determining that an event associated with the workflow has occurred. Such workflow events may relate to patient information, risk information and/or combinations thereof. Exemplary workflow events may include, but are not limited to: a patient's risk score being greater than a predetermined threshold, a patient's risk score increasing more than a predetermined amount over a given time period, and/or a patient being categorized into a particular risk category.

In one embodiment, a patient workflow may comprise transmitting or displaying one or more notifications to various users (e.g., patients, healthcare providers and/or administrators). Each notification may be associated with one or more notification recipients and notification content, such as important patient information, risk information and/or a treatment recommendation. And such notifications may be transmitted in one or more formats, such as but not limited to, push alerts to user devices, SMS messages, emails, phone calls, pages, audible notifications and/or vibrations.

Upon determining that a workflow event has occurred, the system may automatically determine the parties to whom a notification should be sent and transmit the notification to such parties. The system may determine recipients based on any information received and/or stored by the system, such as but not limited to: patient contact information, patient privacy preferences, associations between patients and providers; a type or specialty associated with a provider (e.g., primary care physician, specialist, radiologist, etc.); and/or provider work schedules.

As an example, when a workflow event is detected, the system may alert: one or more on-duty nurse(s), a medical unit clerk, the medical provider of record, and/or anyone else registered to receive alerts for that patient. As another example, the system may only notify the primary care doctor assigned to a particular patient. And as yet another example, the system may only notify the patient.

It will be appreciated that notifications may comprise any content, such as but not limited to: patient information, risk information, a description or prediction of any event(s) that triggered the notification, and/or one or more treatment recommendations. Notifications sent to patients may include an option to contact a particular provider and/or helpful instructions or information (e.g., blood pressure management tips, dietary recommendations, scheduling information, etc.). And notifications sent to providers may include an option to contact the patient and/or additional providers to assist the patient.

In one embodiment, the system may determine and transmit treatment recommendations to providers via notifications. Generally, such treatment recommendations may relate to one or more of: screening the patient for CKD, scheduling an appointment with the patient, referring the patient to a specialist (e.g., a nephrologist), initiating venous access or other interventions to the patient, providing clinical educational materials to the patient, providing a structured diet program to the patient, providing one or more medications to the patient, increasing the patient's medication adherence, ordering one or more lab tests for the patient, improving the patient's blood pressure management, transitioning the patient to planned dialysis enrollment, decreasing or managing the patient's risk of infection, and/or escalating care team assessment.

In one embodiment, a patient workflow may comprise selecting the patient for a clinical trial. For example, patients having a risk score greater than a certain predetermined minimum threshold may be selected as candidates for a clinical trial to assess the efficacy of an intervention, such as administration of a medication, exercise routine and/or dietary program.

In another embodiment, a patient workflow may comprise determining one of a number of possible interventions for a patient based on patient's risk score. In such embodiment, a first intervention may be provided to a patient when their risk score exceeds a certain threshold or a second intervention may be provided to the patient when their risk score is below the threshold. Alternatively, a first intervention may be provided to the patient when they are categorized to a first risk category and a second intervention may be provided to the patient when they are categorized to a second risk category. An exemplary first intervention may comprise administering a first medication and an exemplary second intervention may comprise administering a different, second medication. Alternatively, the first invention may comprise administering a medication and the second intervention may comprise administering a non-medication treatment.

Although not shown, the system may optionally de-identify the patient records by removing identification information therefrom. Generally, patient records may be de-identified to create a secure dataset that can be transferred outside of a health system (e.g., to an external machine learning engine). De-identified patient records may be compliant with the Health Insurance Portability and Accountability Act of 1996 ("HIPAA") (e.g., 45 CFR Parts 160, 162 and 164); however, such records will retain enough information (including any necessary metadata) to allow for effective data analytics. In such embodiments, the system may also re-identify the patient records. For example, the system may re-identify de-identified patient records received from the machine learning engine by restoring any identification information removed therefrom.

Evaluating Patient Outcomes

Figure 2:
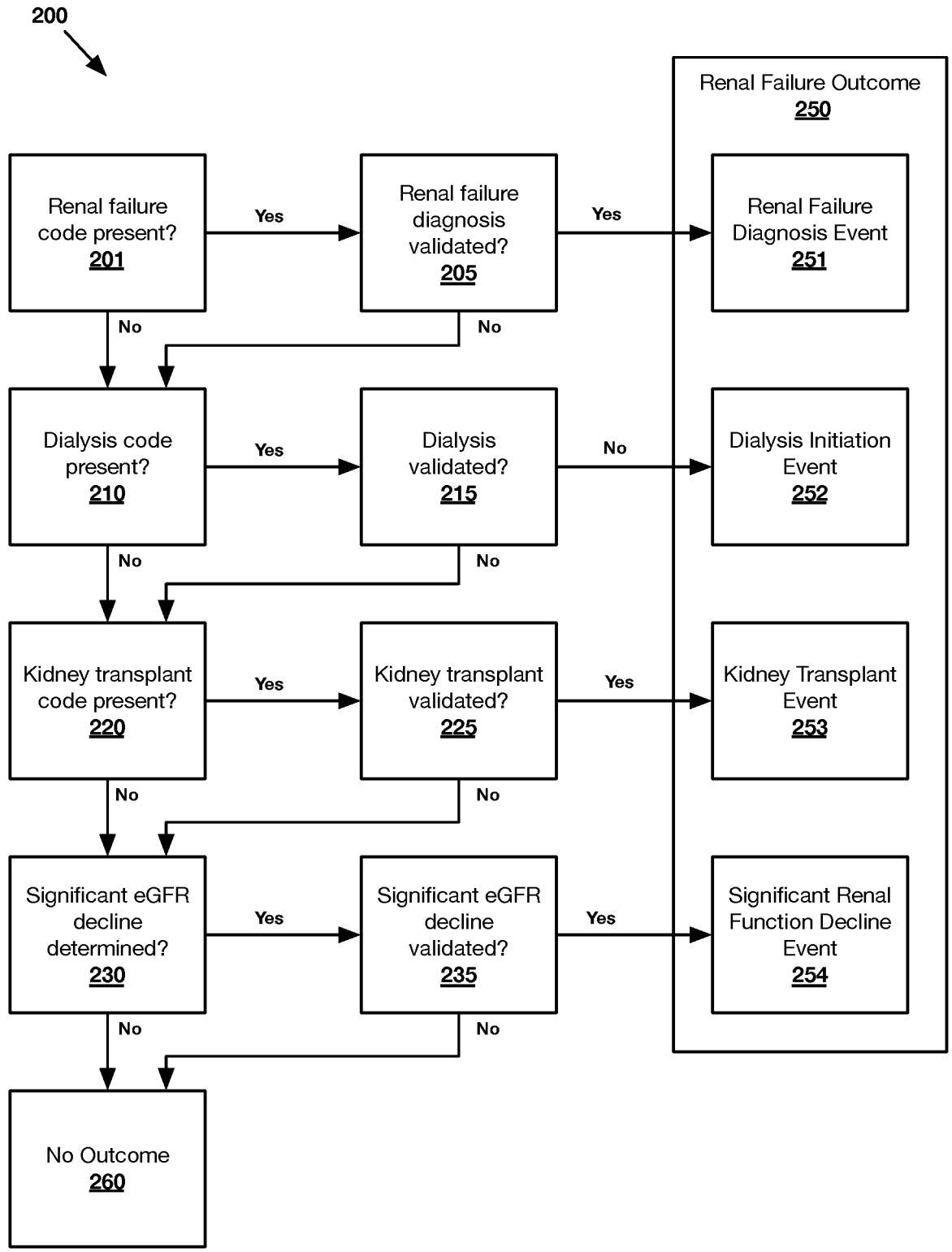
FIG. 2 shows an exemplary method 200 of evaluating a renal failure outcome 280 for any number of patients in accordance with one or more embodiments presented herein.
Figure 3:
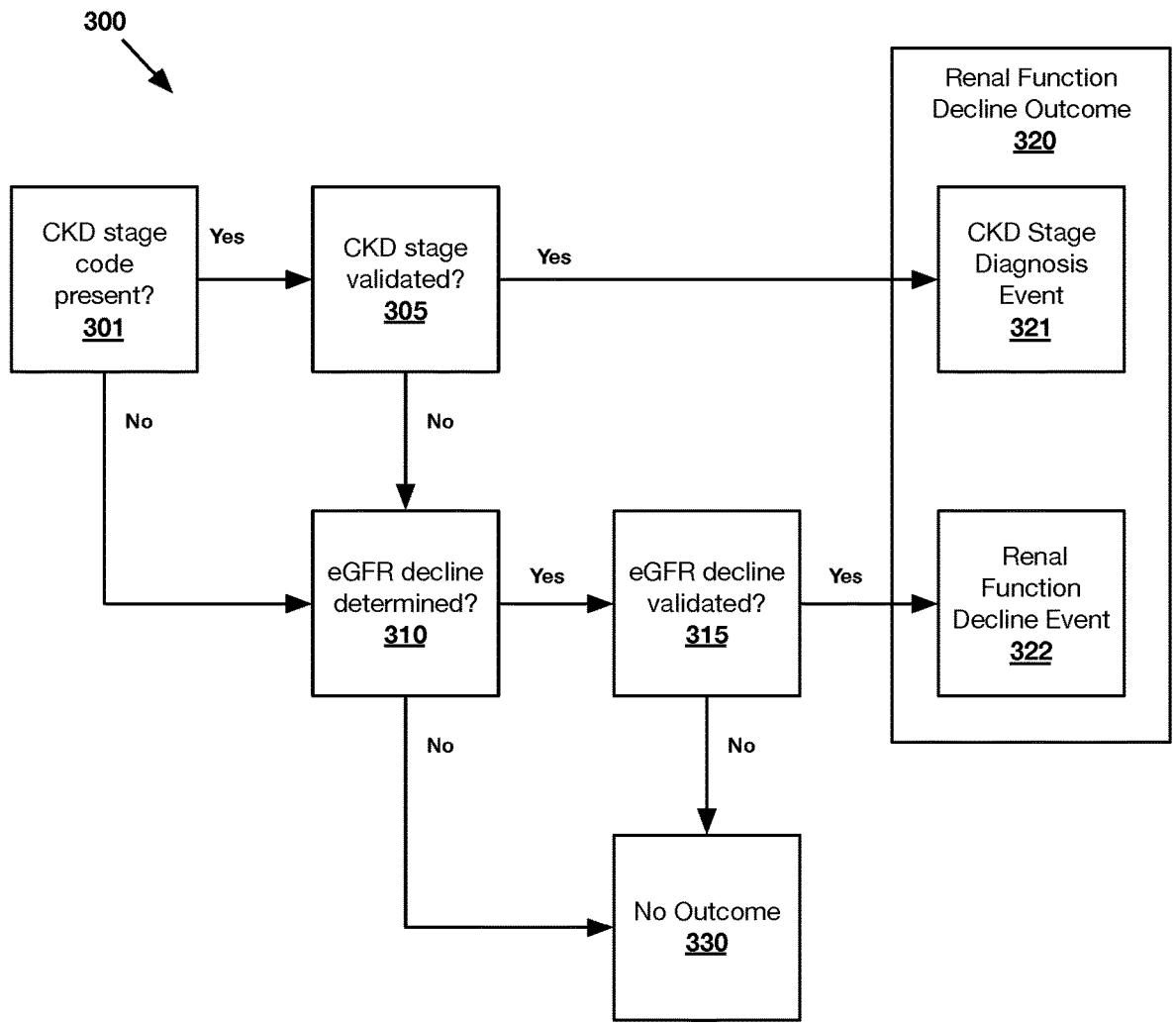
FIG. 3 shows an exemplary method 300 of evaluating a renal function decline outcome 320 for any number of patients in accordance with one or more embodiments presented herein.

Referring to FIGS. 2-3, exemplary methods of evaluating patient outcomes are illustrated. FIG. 2 shows a method 200 for evaluating a renal failure outcome 250. And FIG. 3 shows a method 300 for evaluating a renal function decline outcome, such as a CKD stage 3 outcome or a CKD stage 4 outcome.

It will be appreciated that the various patient outcomes described herein may be satisfied when a patient's renal function declines to at least the level required by the outcome. For example, a CKD stage 4 outcome is satisfied when a patient's renal function declines to at least CKD stage 4; a patient whose renal function declines below CKD stage 4 (e.g., to renal failure) satisfies the outcome. To be clear, a patient who experiences renal function decline to only CKD stage 3 will not satisfy the CKD stage 4 outcome.

As discussed below, the embodiments may employ composite outcomes that combine any number of patient endpoints and may include validation and verification checks to enable highly reliable determinations relating to such outcomes. The composite outcomes may combine various endpoints in a robust phenotype to ensure a patient has truly reached the outcome; patients subject to miscoding and/or who have suffered only an acute—rather than chronic—condition may be excluded.

Referring to FIG. 2, an exemplary method 200 of evaluating a renal failure outcome 250 is illustrated. As shown, the renal failure outcome 250 may be defined by a plurality of events representing potential endpoints, such as a diagnosis event 251; a dialysis initiation event 252; a kidney transplant event 253; and a significant renal function decline event 254.

In order to determine a diagnosis event 251, the system may first identify one or more DP codes relating to renal failure in a patient record 201. Exemplary renal failure codes may include those relating to CKD stage 5 and/or ESRD (e.g., ICD-9-CM 585.5, ICD-10-CM N18.5, ICD-10-CM 112.0 ICD-9-CM 585.6 and ICD-10-CM N18.6).

Upon identifying a renal failure code, the system may employ one or more validation techniques to confirm that the code represents a true diagnosis of renal failure 205. In one embodiment, the system may validate an identified renal failure code by performing a lab value trend analysis. For example, the system may calculate the patient's average eGFR over a period extending from about 15 days to about 185 days from the date of the ESRD code (e.g., about 90 days). The system may then confirm that the average eGFR value is less than 15 ml/min/1.73 m$^2$. In another embodiment, ESRD validation may additionally or alternatively require the presence of additional DP codes or a combination of other endpoints.

Upon validating the renal failure diagnosis at step 205, the system determines that the record satisfies the diagnosis event 251 and, therefore, the patient is considered to satisfy the renal failure outcome 250. However, if the system fails to identify a renal failure code or cannot validate the diagnosis, the patient record is not considered to satisfy the renal failure diagnosis event 251. In such cases, additional outcome endpoints may be analyzed.

As shown, a dialysis initiation event 252 corresponding to a patient beginning dialysis care may also be considered when evaluating the renal failure outcome 250. In determining such event 252, the system may first identify one or more DP codes relating to dialysis 210 in the patient record. Exemplary dialysis DP codes may include, but are not limited to: CPT 90935 ("Hemodialysis procedure with single evaluation by a physician or other qualified healthcare professional"); CPT 90937 ("Hemodialysis procedure requiring repeated evaluation(s) with or without substantial revision of dialysis prescription"); CPT 90945 ("Dialysis procedure other than hemodialysis (e.g., peritoneal dialysis, hemofiltration, or other continuous renal replacement therapies), with single evaluation by a physician or other qualified healthcare professional"); and/or CPT 90947 ("Dialysis procedure other than hemodialysis (e.g., peritoneal dialysis, hemofiltration, or other continuous renal replacement therapies) requiring repeated evaluations by a physician or other qualified healthcare professional, with or without substantial revision of dialysis prescription").

Upon identifying a dialysis code, the system may employ one or more validation techniques 215 to validate dialysis. In one embodiment, the system may exclude dialysis procedures used to treat an AKI. For example, the system may confirm that a DP code relating to an AKI is not present within about 7 days to about 30 days of a dialysis code. As another example, the system may confirm that the patient's eGFR level remains below a given threshold value and is not recovered indicating an acute event For example, the system may calculate the patient's average eGFR over a period of about 15 days to about 185 days from the date of the dialysis procedure code (e.g., about 90 days). The system may then confirm that the average eGFR value remains less than a threshold value of from about 10 to about 20 ml/min/1.73 m$^2$ (e.g., about 15 ml/min/1.73 m2).

As yet another example, the system may employ lab value trend analysis to confirm that a moving average eGFR trend remains below a predetermined minimum value over a time period after the code is assigned. Additionally or alternatively, the system may confirm that the patient's eGFR remains below about 15 ml/min/1.73 m$^2$ for a certain amount of time after the code was assigned (e.g., 90 days).

In another embodiment, the system may identify the location where the dialysis code was entered and determine where such location performs dialysis. And, in yet another embodiment, the system may cross-reference the dialysis DP code with other valid outcome criteria.

Upon validating the dialysis code at step 215, the system determines that the record satisfies the dialysis initiation event 252 and, therefore, the patient is considered to satisfy the renal failure outcome 250. However, if the system fails to identify a dialysis code or cannot validate dialysis, the patient record is not considered to satisfy the dialysis initiation event 252. In such cases, additional outcome endpoints may be analyzed.

As shown, a kidney transplant event 253 corresponding to a patient receiving a kidney transplant may also be considered when evaluating the renal failure outcome 250. In determining such event 253, the system may first identify one or more corresponding DP codes 220, such as but not limited to: CPT 50360 ("Renal allotransplantation, implantation of graft; without recipient nephrectomy"); CPT 50365 ("Renal allotransplantation, implantation of graft; with recipient nephrectomy"); ICD 0TY00Z0 ("Transplantation of right kidney, allogeneic, open approach"); and/or ICD 0TY10Z0 ("Transplantation of left kidney, allogeneic, open approach").

Although it has been found that healthcare provider coding of kidney transplants is generally accurate, further validation may be employed 225. For example, the system may confirm that the patient did not donate a kidney.

Upon successfully validating a kidney transplant at step 225, the system determines that the record satisfies the kidney transplant event 253 and, therefore, the patient is considered to satisfy the renal failure outcome 250. However, if the system fails to identify a kidney transplant code or cannot validate the transplant, the patient record is not considered to satisfy the kidney transplant event 252. In such cases, additional outcome endpoints may be analyzed.

Finally, a significant renal function decline event 254 may also be considered when evaluating the renal failure outcome 250. In one embodiment, the system may determine a significant eGFR decline 230 when a patient's eGFR value is determined to be less than a predetermined minimum value, which is set at 15 ml/min/1.73 m$^2$ in most cases.

In another embodiment, the system may additionally or alternatively determine a significant eGFR decline 230 when the patient's eGFR value decreases by at least a certain amount from a baseline value over a time period. For example, a significant eGFR decline may require a decline from baseline of at least about 30%, at least about 35%, at least about 40% or at least about 45% within the time period. As another example, such decline may be required to occur over a time period of about 2 years, about 2.5 years, about 3 years, about 3.5 years, about 4 years, about 4.5 years or about 5 years. In one particular embodiment, a significant eGFR decline may require a 40% decline in eGFR value from baseline within about 2 years to about 3 years. A 40% decline in eGFR (renal function) in 2-3 years is a broadly accepted surrogate end point for the development of kidney failure in clinical trials of kidney disease progression. See, e.g., Levey A S, et al., "GFR decline as an end point for clinical trials in CKD: a scientific workshop sponsored by the National Kidney Foundation and the US Food and Drug Administration," Am. J. Kidney Dis. 64:6 (2014) pp. 821-35 (incorporated by reference herein in its entirety).

At step 235, the system validates the significant eGFR decline. For example, the system may validate that the eGFR remains below the threshold (within an acceptable error limit) or that the eGFR trend is not recovered (does not decline by about 40% and later recover about 10%, which would only represent a true 30% decline).

Generally, such validation is necessary to exclude acute events. For example, a patient may experience a decline in renal function due to an acute medical event and then the renal function subsequently recovers, which would not represent an end point. Other work in the field of risk prediction for CKD and renal failure has been particularly susceptible to the misclassification of acute events as renal failure events or the mislabeling of events the above validation ensures the model is always predicting on a real world outcome.

Upon verifying the significant eGFR decline 235, the system determines that the patient satisfies the significant renal function decline event 254 and, therefore, the patient is considered to satisfy the renal failure outcome 250. However, if a significant eGFR decline is not determined or verified, the patient is not considered to satisfy the event 254. It will be appreciated that patients who do not satisfy any of the endpoint events (251-254) of the outcome 250 will be considered not to satisfy the renal failure outcome (i.e., no outcome 260).

In the illustrated embodiment, an outcome of patient death is not be considered. This is due to the limitations of EHR data and the fact that the disclosed embodiments focus on calculating short-term risk for patients (e.g., over periods extending a few months to a few years). Of course, other outcome definitions may include patient death events.

Referring to FIG. 3, an exemplary method of evaluating a renal function decline outcome 320 is illustrated. As shown, the outcome 320 is defined by a plurality of events representing potential endpoints, such as a CKD stage diagnosis event 321 and a renal function decline event 322.

In order to determine a CKD stage diagnosis event 321, the system may first identify one or more DP codes relating to a certain CKD stage 301. For a CKD stage 3 outcome, such codes may include ICD-9-CM 585.3 and/or ICD-10-CM N18.3. And for CKD stage 4 outcome, such codes may include ICD-9-CM 585.4 and/or ICD-10-CM N18.4.

The system may optionally employ one or more validation techniques to confirm that the code represents a true diagnosis of the CKD stage 305. In one embodiment, the system may validate the CKD stage diagnosis 305 by evaluating the renal function decline event 322 described below. In other embodiments, the system may confirm the presence of one or more additional DP codes.

Upon identifying a CKD stage code 301 and optionally validating the CKD stage diagnosis 305, the system determines that the patient record satisfies the CKD stage diagnosis event 321 and, therefore, the patient is considered to satisfy the renal function decline outcome 320. Otherwise, the patient record is not considered to satisfy the event 321 and additional outcome endpoints may be analyzed.

As shown, the system may evaluate a renal function decline event 322 relating to a sustained decline in a patient's renal function 310. In one embodiment, the system may determine sustained eGFR decline 310 by calculating the patient's average eGFR (as discussed above) and confirming that the value is within a certain range. For example, the system may confirm that the average eGFR value is from 30 to less than 60 ml/min/1.73 m² for a CKD stage 3 outcome. As another example, the system may confirm that the average eGFR value is from 15 to less than 30 ml/min/1.73 m² for a CKD stage 4 outcome.

At step 315, the system validates the eGFR decline, for example, to exclude acute events. As discussed above, the system may confirm that the patient's eGFR value remains within the relevant range (within an acceptable error limit), over a certain period of time (e.g., 90 days). Additionally or alternatively, the system may confirm the presence or absence of one or more additional DP codes.

Upon determining and validating eGFR decline, the system determines that the patient satisfies the renal function decline event 322 and, therefore, the patient is considered to satisfy the renal function decline outcome 320. However, if eGFR decline is not determined or otherwise does not pass validation, the patient is not considered to satisfy the event 322. It will be appreciated that patients who do not satisfy any of the endpoint events (321-322) of the outcome 320 will be considered not to satisfy the renal function decline outcome (i.e., no outcome 330).

Model Performance

In order to employ a machine learning system in clinical practice, a risk threshold must be selected where the system executes a given patient workflow only for patients associated with a risk score that is higher than the threshold. It will be appreciated that, as the risk threshold is increased, the number of false-positives will decrease, but the number of false-negatives will increase. Conversely, as the threshold is decreased, the number of false-positives increases, but the number of false-negatives increases. Accordingly, assessing the optimal threshold for a given workflow involves deciding on an appropriate tradeoff between false-positive and false-negative results.

In the context of the current embodiments, there is generally a large penalty for false-negatives and a small penalty for false negatives. As an example, consider a workflow that transmits a notification to a provider including a treatment recommendation to provision venous access in a patient determined to be at risk for renal failure. In this case, failing to identify an at-risk patient (i.e., a false-negative) may result in the patient crashing onto dialysis, while incorrectly identifying a patient (i.e., a false-positive) may result in the provider unnecessarily provisioning venous access to the patient. Although the penalty for the false-negative is larger than that for the false-positive, it will be appreciated that venous access is an expensive medical procedure that should not be undertaken lightly; a balance must be struck.

Moreover, to correctly assess the clinical validity of a model it is important to examine many outcomes over time—not just outcomes inside a prediction window. For example, a model may associate a negative result to a patient who reaches an outcome a day after the prediction end date, whereas the clinical reality is that this represents a patient who should be treated. Accordingly, in certain embodiments, the proportional hazard curve may be analyzed. The proportional hazard curve curve shows the percentage of the population who have not yet reached the outcome at a given threshold against time. Close evaluation of hazard curves at different model thresholds allows providers to set an intervention threshold at a level where a valuable percentage of the population will experience the outcome within a timeframe, where the intervention remains clinically efficacious.

A number of metrics may be calculated to assess the performance of the disclosed models, including AUC of the ROC curve, sensitivity (recall), specificity and model coverage. AUC is a universal diagnostic for predictive models that summarizes the predictive performance across a full range of score thresholds. Confidence intervals ("CIs") for AUCs may be calculated using the approach described in McNeil, B J et al., "Statistical Approaches to the Analysis of Receiver Operating Characteristic (ROC) Curves," Medical Decision Making 4:2 (1984) pp. 137-50 (incorporated by reference herein in its entirety).

As shown in Equation 1, below, sensitivity (i.e., recall or true-positive rate) corresponds to the Y-axis of the ROC curve, where each point corresponds to a threshold at which a prediction is made. Sensitivity provides the percentage of patients who are correctly identified as having a condition for some predictive threshold. For example, sensitivity may indicate that 95% of the top 20% of scored patients are associated with an identified outcome. It will be appreciated that a higher sensitivity corresponds to a lower prediction threshold, which in turn reflects a preference to avoid false negatives over false positives.

$$\text{Sensitivity} = \frac{|\{\text{valid outcomes}\} \cap \{\text{predicted outcomes}\}|}{|\{\text{valid outcomes}\}|} \quad (1)$$

As shown in Equation 2, below, specificity (i.e., true-negative rate) is the cousin of sensitivity (Equation 1) and measures the proportion of actual negatives that are correctly identified below a given score threshold (and 1-specificity corresponds to the X-axis of the ROC curve).

$$\text{Precision} = \frac{|\{\text{valid outcomes}\} \cap \{\text{predicted outcomes}\}|}{|\{\text{predicted outcomes}\}|} \quad (2)$$

The disclosed machine learning models may achieve very high levels of performance in predicting risk of various renal-related outcomes in patient populations having widely varying characteristics. For example, the models may be configured to achieve an AUC of about 0.80 to about 0.95. In certain embodiments, the models may be configured to achieve an AUC of at least about 0.8, at least about 0.825, at least about 0.85, at least about 0.875, at least about 0.9, at least about 0.925, or at least about 0.95.

Such models may further achieve a sensitivity and/or specificity within a top quartile of from about 0.7 to about 0.95. In certain embodiments, the models may be configured to achieve a sensitivity and/or specificity within the top quartile of at least about 0.7, at least about 0.75, at least about 0.8, at least about 0.85, at least about 0.9, or at least about 0.95.

Importantly, the disclosed embodiments may achieve such metrics while providing significantly higher patient coverage than conventional risk scoring techniques. For example, the machine learning models may provide risk scores for from about 95% to about 100% of patients, even when labs such as UACR are not included in the patients' records (e.g., at least about 95%, at least about 96%, at least about 97%, at least about 98%, at least about 99% or about 100%). Detailed performance metrics are provided for exemplary models in Examples 1-4, below.

System

Figure 4:
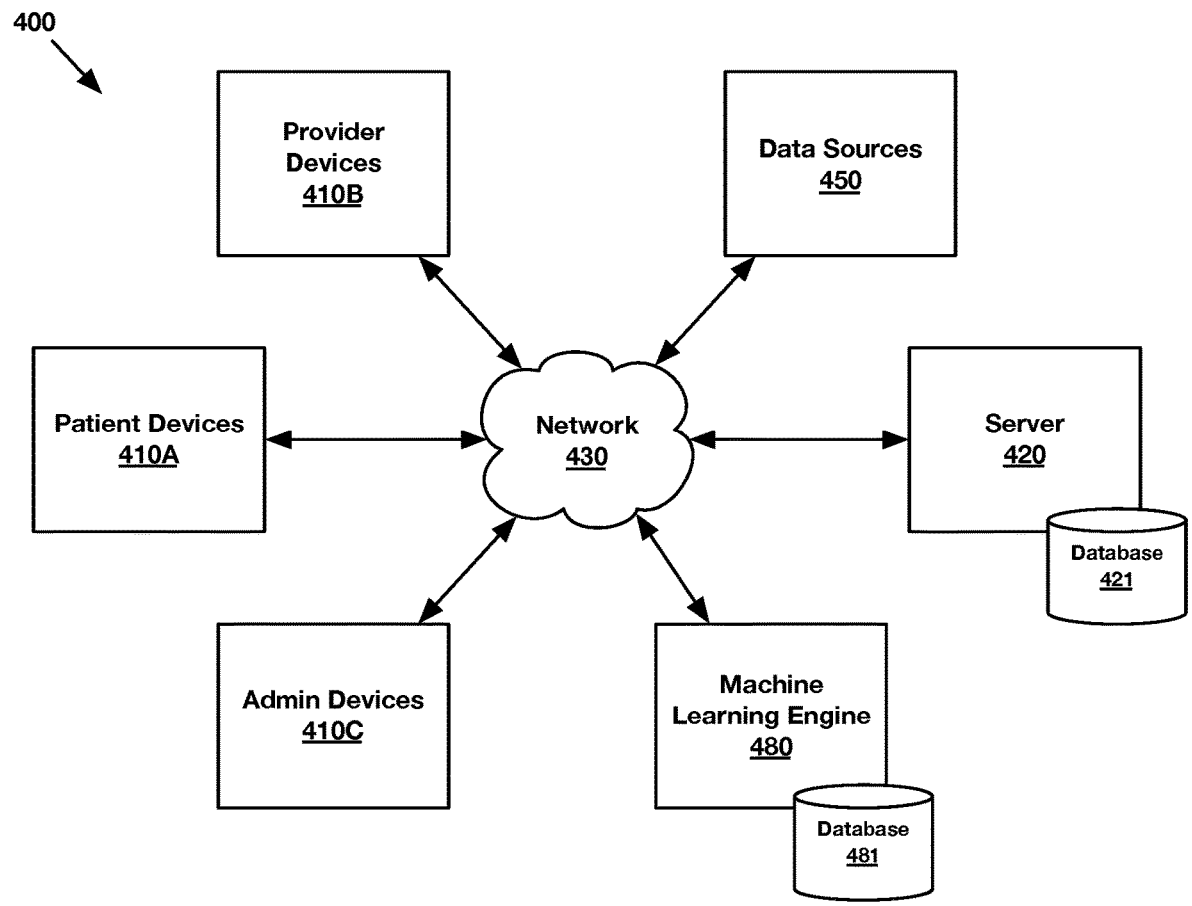
FIG. 4 shows an exemplary system 400 in accordance with one or more embodiments presented herein.

Referring to FIG. 4, an exemplary system 400 according to an embodiment is illustrated. As shown, the system 400 comprises a server 420 in communication with a machine learning engine 480 ("ML engine"), one or more data sources 450 and various client devices (e.g., patient devices 410A, provider devices 410B, and/or admin devices 410C).

Generally, the server 420 may be configured to receive/transmit information from/to various system components, with or without user interaction via a network 430. The server 420 may also be configured to store such information in one or more local or remote databases 421.

In one embodiment, the server 420 may be configured to receive input data from one or more data sources 450 (e.g., via the network 430). As discussed above, data sources 450 may comprise any system that stores electronic patient data. Exemplary data sources 450 may include, but are not limited to, EHR systems, health facility systems, insurance claims systems, medical and/or biometric devices, financial systems and/or others.

Upon receiving input data from a data source 450, the server may process such data into various datasets comprising values of features relating to patient information (as discussed above). Such datasets may then be transmitted (e.g., over the network 430), from the server 420 to the ML engine 480 for further processing.

The ML engine 480 is generally adapted to determine risk information for any number of patient records, update patient records with such risk information, and transmit the updated patient records to the server 420 for further action (e.g., displaying records, transmitting records and/or executing patient workflows). In one embodiment, the ML engine 480 may comprise an internal or external memory (e.g., database 481) to store various information, such as patient records received from the server, determined risk information and/or updated patient records. The ML engine 480 may further utilize such memory to store information that may be employed to create and execute any number of data processing pipelines.

In one embodiment, the ML engine 480 may employ modular data processing pipelines to determine risk information for patient records, wherein each pipeline may be associated with any number of nodes. Generally, a node comprises a dynamic unit of work that may be connected to, or otherwise combined with, other nodes. To that end, each node may be associated with one or more of the following: input or dependency information (e.g., a location and type of input data to be received by the node), output or results information (e.g., a location and type of output data to generated by the node), logic or computational aspects to manipulate input data, scheduling information, a status, and/or a timeout value. It will be appreciated that data nodes can inherit properties from one or more parent nodes, and that the relationships among nodes may be defined by reference.

The ML engine 480 may include various components to manage and execute pipelines, such as a task scheduler, a task runner and/or one or more computing resources (i.e., workers). Generally, these components work together to execute the pipelines by (1) compiling the various pipeline components, (2) creating a set of actionable tasks, (3) scheduling the tasks, and/or (4) assigning such tasks to a computational resource.

In one embodiment, a scheduler may be employed to split operations into a plurality of tasks, wherein each task is associated with at least one input node and at least one output node, and wherein each task comprises a complete definition of work to be performed. The scheduler may also determine scheduling information for each of the tasks in order to specify when a given task should be executed by a worker. For example, tasks may be scheduled to run: on activation, periodically (i.e., at the beginning or end of a predetermined period of time), at a starting time and date, and/or before an ending time and date.

The scheduler may then provide a complete set of tasks and corresponding scheduling information to one or more task runners for processing. Generally, task runners are applications that poll a data pipeline for scheduled tasks and then execute those tasks on one or more machines (workers). When a task is assigned to a task runner, it performs the task and reports its status back to the data pipeline.

It will be appreciated that the execution of computations may be "lazy," such that the organization of nodes can be performed without executing the nodes until explicitly instructed later. It will be further appreciated that, in some embodiments, the ML engine 480 may be agnostic to lower-level computational scheduling that formulates and allocates tasks among computational resources. That is, the platform may employ one or more third-party systems to schedule and execute low-level data manipulations, such as a single computing device or a distributed clusters of computing devices running Apache Spark and/or Apache Hadoop.

As further shown in FIG. 4, any number of users may access the server 420 via various client devices (e.g., patient devices 410A, provider devices 410B and/or admin devices 410C) connected to the network 430. The various client devices may be collectively referred to as "client device 410" for convenience.

Generally, a client device 410 may be any device capable of running a client application and/or of communicating with the server 420 and/or security module 490 (e.g., via a client application or via a web browser). Exemplary client devices 410 may include desktop computers, laptop computers, tablets, smartphones, and/or wearable devices.

The relationship of client 410 and server 420 arises by virtue of computer programs running on the respective computers and having a client-server relationship to each other. Accordingly, each of the client devices 410 may have a client application running thereon, where the client application may be adapted to communicate with a server application running on a server 420, for example, over a network 430. Thus, the client application and server 420 may be remote from each other. Such a configuration may allow users of client applications to input information and/or interact with the server from any location.

As discussed in detail below, one or more client applications may be adapted to present various user interfaces to users. Such user interfaces may be based on information stored on the client device 410 and/or received from the server 420. Accordingly, client applications may be written in any form of programming language, including compiled or interpreted languages, or declarative or procedural languages, and it can be deployed in any form, including as a standalone program or as a module, component, subroutine, or other unit suitable for use in a computing environment. Such software may correspond to a file in a file system. A program can be stored in a portion of a file that holds other programs or data. For example, a program may include one or more scripts stored in a markup language document; in a single file dedicated to the program in question; or in multiple coordinated files (e.g., files that store one or more modules, sub programs, or portions of code).

The client application(s) can be deployed and/or executed on one or more computing devices that are located at one site or distributed across multiple sites and interconnected by a communication network. In one embodiment, a client application may be installed on (or accessed by) one or more client devices 410. It will be apparent to one of ordinary skill in the art that, in certain embodiments, any of the functionality of a client may be incorporated into the server, and vice versa. Likewise, any functionality of a client application may be incorporated into a browser-based client, and such embodiments are intended to be fully within the scope of this disclosure. For example, a browser-based client application could be configured for offline work by adding local storage capability, and a native application could be distributed for various native platforms (e.g., Microsoft Windows™, Apple Mac OS™, Google Android™ or Apple iOS™) via a software layer that executes the browser-based program on the native platform.

In one embodiment, communication between a client application and the server may involve the use of a translation and/or serialization module. A serialization module can convert an object from an in-memory representation to a serialized representation suitable for transmission via HTTP/HTTPS or another transport mechanism. For example, the serialization module may convert data from a native, in-memory representation into a JSON string for communication over the client-to-server transport protocol.

Similarly, communications of data between a client device 410 and the server 420 may be continuous and automatic, or may be user-triggered. For example, the user may click a button or link, causing the client to send data to the server. Alternately, a client application may automatically send updates to the server periodically without prompting by a user. If a client sends data autonomously, the server may be configured to transmit this data, either automatically or on request, to additional clients and/or third-party systems.

Generally, the network 430 may include wide area networks ("WAN"), local area networks ("LAN"), intranets, the Internet, wireless access networks, wired networks, mobile networks, telephone networks, optical networks, or combinations thereof. The network 430 may be packet switched, circuit switched, of any topology, and may use any communication protocol. Communication links within the network 430 may involve various digital or an analog communication media such as fiber optic cables, free-space optics, waveguides, electrical conductors, wireless links, antennas, radio-frequency communications, and so forth.

Figure 5:
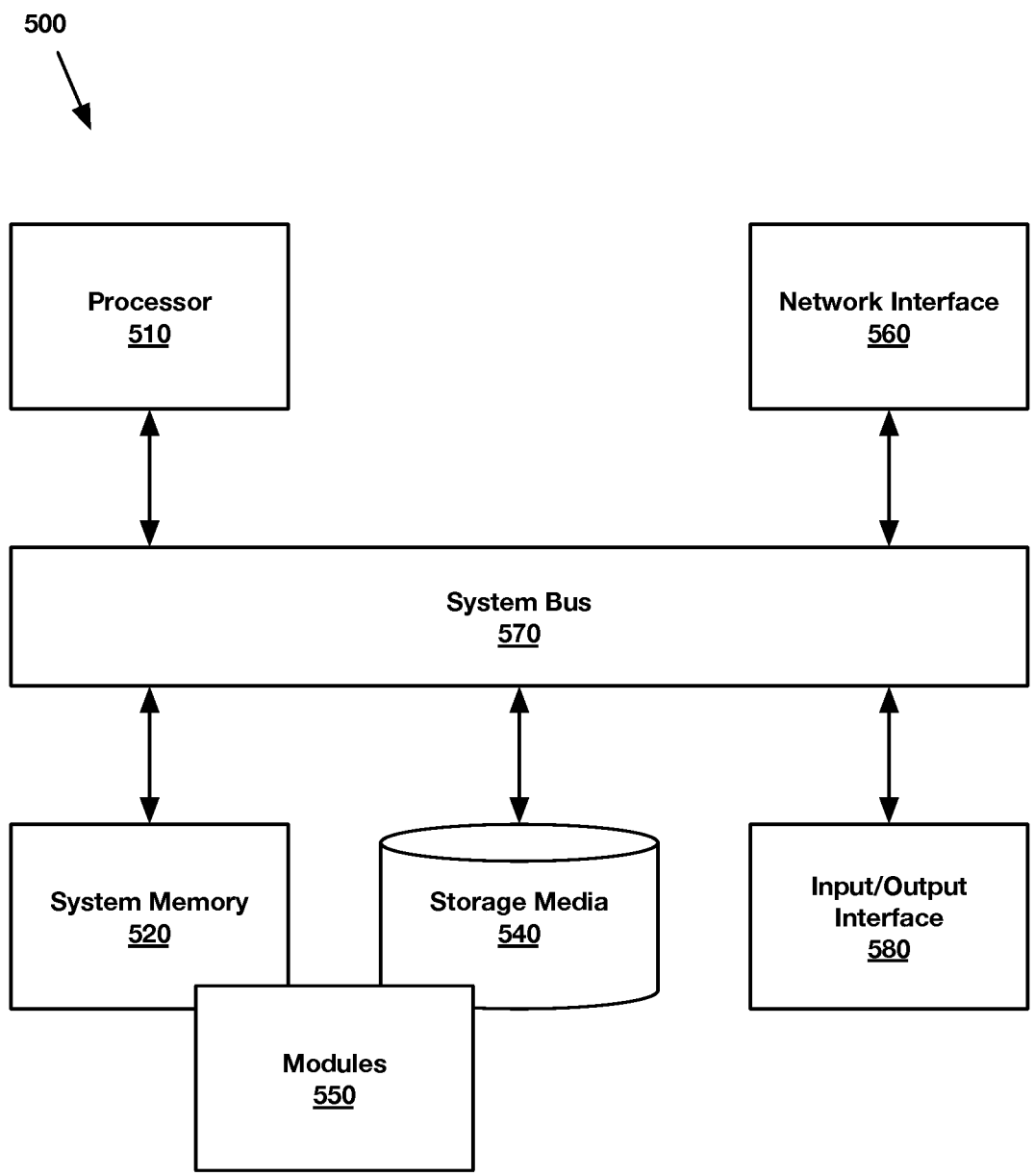
FIG. 5 shows an exemplary computing device 500 and modules 550 in accordance with one or more embodiments presented herein.

Referring to FIG. 5, a block diagram is provided illustrating a computing device 500 and modules 550 in accordance with one or more embodiments presented herein. The computing device 500 may correspond to any of the various computers, servers, mobile devices, embedded systems, or computing systems presented herein (e.g., the client device(s) 410, server(s) 420, and/or data source(s) 450 of FIG. 4). And the modules 550 may comprise one or more hardware or software elements configured to facilitate the computing device(s) 500 in performing the various methods and processing functions presented herein.

The computing device 500 may comprise all kinds of apparatuses, devices, and machines for processing data, including but not limited to, a programmable processor, a computer, and/or multiple processors or computers. For example, the computing device 500 may be implemented as a conventional computer system, an embedded controller, a laptop, a server, a mobile device, a smartphone, a tablet, a wearable device, a kiosk, one more processors associated with a display, a customized machine, any other hardware platform and/or combinations thereof. Moreover, a computing device may be embedded in another device, such as the above-listed devices and/or a portable storage device (e.g., a universal serial bus ("USB") flash drive). In some embodiments, the computing device 500 may be a distributed system configured to function using multiple computing devices interconnected via a data network or system bus 570.

As shown, an exemplary computing device 500 may include various internal and/or attached components, such as a processor 510, system bus 570, system memory 520, storage media 540, input/output interface 580, and network interface 560 for communicating with a network.

The processor 510 may be configured to execute code or instructions to perform the operations and functionality described herein, manage request flow and address mappings, and to perform calculations and generate commands. The processor 510 may be configured to monitor and control the operation of the components in the computing device 500. The processor 510 may be a general-purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 510 may be a single processing unit, multiple processing units, a single processing core, multiple processing cores, special purpose processing cores, coprocessors, or any combination thereof. In addition to hardware, exemplary apparatuses may comprise code that creates an execution environment for the computer program (e.g., code that constitutes one or more of: processor firmware, a protocol stack, a database management system, an operating system, and a combination thereof). According to certain embodiments, the processor 510 and/or other components of the computing device 500 may be a virtualized computing device executing within one or more other computing devices.

The system memory 520 may include non-volatile memories such as read-only memory ("ROM"), programmable ROM, erasable programmable ROM, flash memory, or any other device capable of storing program instructions or data with or without applied power. The system memory 520 also may include volatile memories, such as various types of random-access memory ("RAM"). The system memory 520 may be implemented using a single memory module or multiple memory modules. While the system memory is depicted as being part of the computing device 500, one skilled in the art will recognize that the system memory may be separate from the computing device without departing from the scope of the subject technology. It should also be appreciated that the system memory may include, or operate in conjunction with, a non-volatile storage device such as the storage media 540.

The storage media 540 may include a hard disk, a compact disc, a digital versatile disc ("DVD"), a Blu-ray disc, a magnetic tape, a flash memory, other non-volatile memory device, a solid-state drive ("SSD"), any magnetic storage device, any optical storage device, any electrical storage device, any semiconductor storage device, any physical-based storage device, any other data storage device, or any combination/multiplicity thereof. The storage media 540 may store one or more operating systems, application programs and program modules such as module, data, or any other information. The storage media may be part of, or connected to, the computing device 500. The storage media may also be part of one or more other computing devices that are in communication with the computing device such as servers, database servers, cloud storage, network attached storage, and so forth.

The modules 550 may comprise one or more hardware or software elements configured to facilitate the computing device 500 with performing the various methods and processing functions presented herein. The modules 550 may include one or more sequences of instructions stored as software or firmware in association with the system memory 520, the storage media 540, or both. The storage media 540 may therefore represent examples of machine or computer readable media on which instructions or code may be stored for execution by the processor. Machine or computer readable media may generally refer to any medium or media used to provide instructions to the processor. Such machine or computer readable media associated with the modules may comprise a computer software product. It should be appreciated that a computer software product comprising the modules may also be associated with one or more processes or methods for delivering the module to the computing device via the network, any signal-bearing medium, or any other communication or delivery technology. The modules 550 may also comprise hardware circuits or information for configuring hardware circuits such as microcode or configuration information for an FPGA or other PLD.

The input/output ("I/O") interface 580 may be configured to couple to one or more external devices, to receive data from the one or more external devices, and to send data to the one or more external devices. Such external devices along with the various internal devices may also be known as peripheral devices. The I/O interface 580 may include both electrical and physical connections for operably coupling the various peripheral devices to the computing device 500 or the processor 510. The I/O interface 580 may be configured to communicate data, addresses, and control signals between the peripheral devices, the computing device, or the processor. The I/O interface 580 may be configured to implement any standard interface, such as small computer system interface ("SCSI"), serial-attached SCSI ("SAS"), fiber channel, peripheral component interconnect ("PCI"), serial bus, parallel bus, advanced technology attachment ("ATA"), serial ATA ("SATA"), USB, Thunderbolt, FireWire, various video buses, and the like. The I/O interface may be configured to implement only one interface or bus technology. Alternatively, the I/O interface may be configured to implement multiple interfaces or bus technologies. The I/O interface may be configured as part of, all of, or to operate in conjunction with, the system bus 570. The I/O interface 480 may include one or more buffers for buffering transmissions between one or more external devices, internal devices, the computing device 500, or the processor 510.

The I/O interface 580 may couple the computing device 500 to various input devices including mice, touch-screens, scanners, biometric readers, electronic digitizers, sensors, receivers, touchpads, trackballs, cameras, microphones, keyboards, any other pointing devices, or any combinations thereof. When coupled to the computing device, such input devices may receive input from a user in any form, including acoustic, speech, visual, or tactile input.

The I/O interface 580 may couple the computing device 500 to various output devices such that feedback may be provided to a user via any form of sensory feedback (e.g., visual feedback, auditory feedback, or tactile feedback). For example, a computing device can interact with a user by sending documents to and receiving documents from a device that is used by the user (e.g., by sending web pages to a web browser on a user's client device in response to requests received from the web browser). Exemplary output devices may include, but are not limited to, displays, speakers, printers, projectors, tactile feedback devices, automation control, robotic components, actuators, motors, fans, solenoids, valves, pumps, transmitters, signal emitters, lights, and so forth. And exemplary displays include, but are not limited to, one or more of: projectors, cathode ray tube ("CRT") monitors, liquid crystal displays ("LCD"), light-emitting diode ("LED") monitors and/or organic light-emitting diode ("OLED") monitors.

Embodiments of the subject matter described in this specification can be implemented in a computing device 500 that includes one or more of the following components: a backend component (e.g., a data server); a middleware component (e.g., an application server); a frontend component (e.g., a client computer having a graphical user interface ("GUI") and/or a web browser through which a user can interact with an implementation of the subject matter described in this specification); and/or combinations thereof. The components of the system can be interconnected by any form or medium of digital data communication, such as but not limited to, a communication network. Accordingly, the computing device 500 may operate in a networked environment using logical connections through the network interface 560 to one or more other systems or computing devices across a network.

The processor 510 may be connected to the other elements of the computing device 500 or the various peripherals discussed herein through the system bus 570. It should be appreciated that the system bus 570 may be within the processor, outside the processor, or both. According to some embodiments, any of the processor 510, the other elements of the computing device 500, or the various peripherals discussed herein may be integrated into a single device such as a system on chip ("SOC"), system on package ("SOP"), or ASIC device.

Client Applications

As discussed above, the system may comprise one or more client applications. Exemplary client applications may include, but are not limited to, a data management application, a patient information visualization application and/or a machine learning engine administration application.

A data management application may be provided to allow administrative users to create and update data processing pipelines. This application may allow users to specify information such as: connections to various data sources (e.g., via input of data source information), how raw input data should be processed and formatted, where various data should be stored, etc. In certain embodiments, the data management application may comprise or otherwise connect to various coding systems in order to allow for codes to be grouped into clean, comprehensive sets (e.g., DP codes, lab test codes, medications codes, costs codes, revenue codes, SNOMED etc.). Optionally, the data management application may comprise or otherwise communicate with a patient records de-identification application for use in removing identification information from patient records A patient information visualization application may display various user interface elements to allow administrative users and/or providers to view longitudinal patient information over time. In one embodiment, this application may allow users to search a patient population to find patients who match specific criteria (e.g., demographics, lab test values, medication usage, etc.). In another embodiment, this application may allow users to create various reports comprising charts, graphs, tables, and/or other components relating to user-defined outcomes.

A machine learning engine administration application may also be provided to allow users to create and update various ML models and any algorithms, features and/or weights associated therewith. This application may also allow users to investigate model and/or feature performance. In one embodiment, such application may comprise or otherwise be connected to a classification library application such that custom patient groupings may be created and analyzed. Additionally or alternatively, this application may comprise functionality for creating and modifying patient workflows (e.g., workflow rules) and for managing and tracking patients associated with such workflows.

Figure 6:
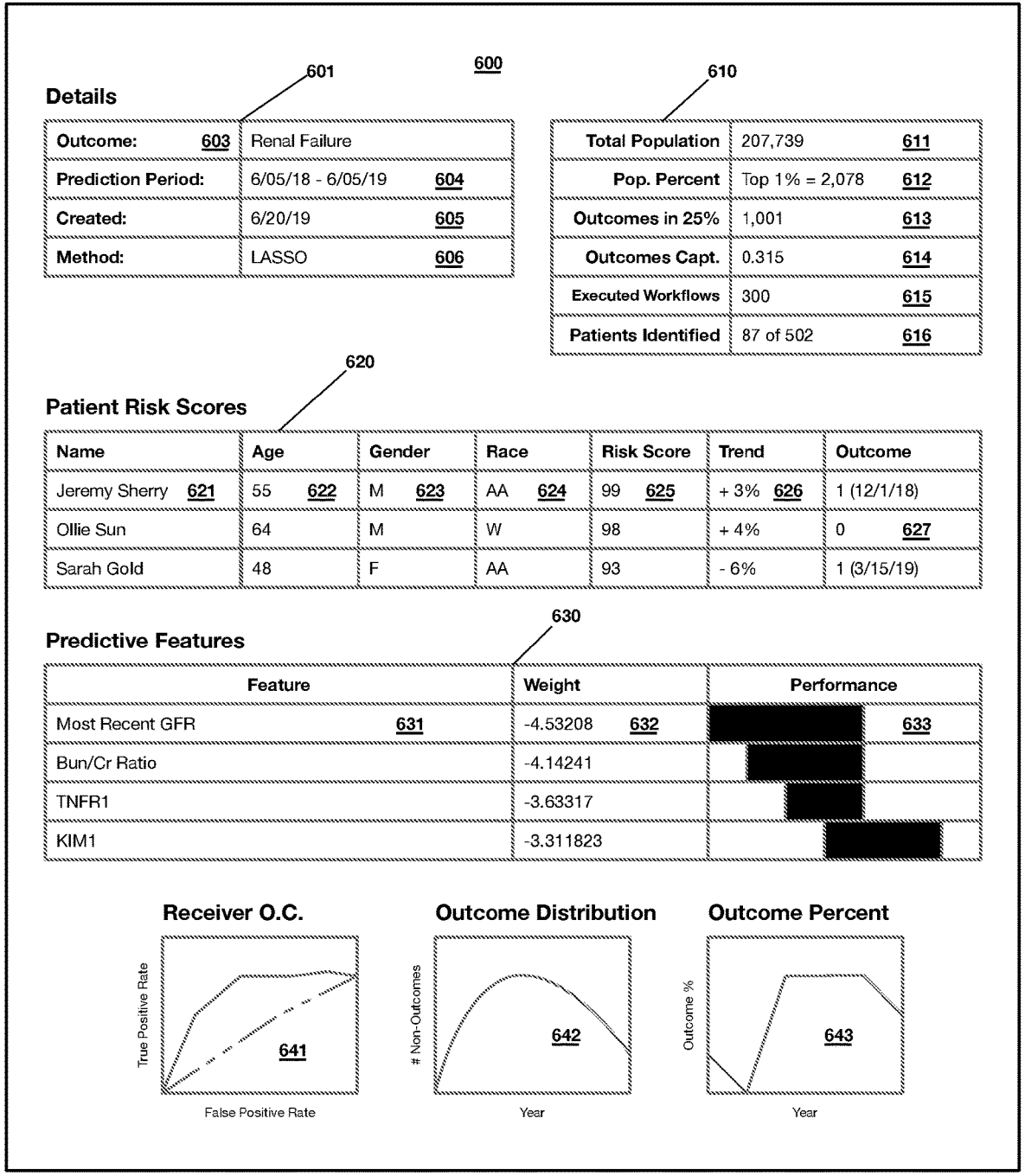
FIG. 6 shows an exemplary user interface screen 600 of a client application in accordance with one or more embodiments presented herein.

Referring to FIG. 6, an exemplary user interface screen 600 of a ML engine administration application is illustrated. As shown, the screen may display various risk information determined by the ML engine for patient records and/or information relating to performance of the ML engine. In one embodiment, this screen 600 may display a details table 601, a patient risk scores table 620, and a features table 630.

In one embodiment, the screen 600 may include information about the predictive engine itself and the input data analyzed by the ML engine. For example, the screen may display: the target event/outcome 603 for which risk information was determined (e.g., renal failure), the corresponding prediction period 604 (e.g., 1 year), a date the risk information was determined 605, and the model that was employed by the ML engine to determine such information 606.

The disclosed embodiments may be utilized to determine optimal patient cohort groupings, as well as to determine how various patient information may be combined in order to generate a risk categorization in an optimal or near-optimal manner (e.g., correctly predicting renal outcomes with a low false-positive rate). Accordingly, the screen 600 may display the total number of unique patients included in the input data 611, the number of patients associated with a top risk percentage 612 (i.e., patients associated with a risk score having a value that is in the top 1% of all risk scores for the given patient cohort). The screen may further display the total number of patients within the risk category who actually experience the outcome 613, the percent of outcomes captured within the risk category 614, the number of patients for whom a workflow was executed 615 (e.g., notifications sent to notify providers that patients should be enrolled for an effective intervention program) and the number of identified patients who have had an outcome 616.

In other embodiments, the screen 600 may display additional information about the risk model broken out according to various risk categories, wherein each category is associated with a risk percentage (e.g., top 0.01% risky patients, top 0.05% risky patients, top 0.1% risky patients, top 0.15% risky patients, top 0.2% risky patients, top 0.25% risky patients, top 0.5% risky patients, top 0.75% risky patients, top 1% risky patients, top 2.5% risky patients, top 5% risky patients, top 10% risky patients, etc.). In one embodiment, category information for each risk category may comprise: total number of patients associated with the risk category, total number of patients in the risk category who experienced the outcome, positive predictive value ("PPV") for the risk category, negative predictive value ("NPV") for the risk category, sensitivity (recall) for the risk category, and/or specificity for the risk category.

As shown, this screen 600 may also display a patient risk scores table 620, which shows the patients who were determined to have the highest probability of experiencing the outcome (i.e., patients with the highest risk score). The table may display some or all of the following information for each patient: name 621, age 622, race 623, gender, contact information, risk score 625 (and/or probability), the trend over a predetermined period of time of the patient's risk score 625, and/or outcome information 627 (e.g., whether or not the patient experienced the outcome within the outcome period and, if so, the date of the outcome).

In one embodiment, the screen may also display a features table 630, which shows important patient information features 631 employed by the ML engine to determine risk information. In one embodiment, the table may include information relating to the performance of each feature 633 and/or the feature weight 632 corresponding to each feature to determine risk information.

Finally, the screen 600 may also display various graphical interface elements providing information about the performance of the risk model. For example, the screen may display a graph 641 showing the ROC curve and corresponding AUC for the selected model; an outcome distribution graph 642 showing the total number of non-outcomes per year; and an outcome percent graph 643 depicting the percentage of adverse outcomes per year.

EXPERIMENTS

Experiment 1

In Experiment 1, a machine learning system comprising a LASSO regression machine learning model was employed to predict risk of renal failure using electronic patient data from multiple EHR systems. Various time frame constraints were tested to evaluate the ML model's ability to determine clinically actionable risk information for patients, such as recommending early, yet timely, nephrology consultations for at-risk patients and providing notifications to practitioners regarding at-risk patients to allow for coordination of care transitions among different practice settings. The ML model was also compared to the traditional KFRE model, which requires age, sex, eGFR and at least one UACR lab test value to output a score. As discussed below, the ML model achieved superior predictive performance and vastly improved patient coverage.

Input data was ingested from two data sources—an EHR system associated with the Icahn School of Medicine at Mount Sinai CKD Registry (the "CKDR dataset") and an EHR system associated with the Center for Health Systems Innovation at Oklahoma State University provided by the Cerner Corporation (the "CHSI dataset"). The CKDR dataset was curated to include only patient records that met the following criteria: (1) at least two eGFR values of less than 60 ml/min/1.73 m² were determined for the patient more than 90 days apart; (2) at least two UACR values greater than 30 mg/g were determined for the patient more than 90 days apart; and/or (3) the patient was associated with at least one DP code indicative of CKD (e.g., ICD-10-CM N18.4), ESRD (e.g., ICD-10-CM N18.6), polycystic kidney disease (e.g., ICD-10-CM Q61.3), glomerulonephritis (e.g., ICD-10-CM 580.4), diabetic nephropathy (e.g., ICD-10-CM E11.21), hypertensive nephrosclerosis (e.g., ICD-10-CM 112.9) or renovascular disease (e.g., ICD-10-CM 115.0). And the CHSI dataset was curated to include only patients with CKD and/or CHF by selecting patient records that met one or more of the following criteria: (1) an eGFR value of less than 60 ml/min/1.73 m² was determined for the patient; or (2) at least three visits were recorded before the patient received a first diagnosis of CHF.

Machine learning models were devised to target the individual risk of renal failure within twelve months of each patient's first calculated eGFR result of less than 60 ml/min/1.73 m², where the outcome occurred after the patient's first recorded DP code. A model design choice was made to concentrate on calculating the twelve month risk with a view to prioritizing the need for patients that should receive immediate nephrology consultation.

Features were created, as discussed above, relating to each patient's demographics information, DP information, lab tests information, and medications information. And ML model validation was performed by combining the two datasets and employing a 75/25 split of the full population to create training and validation cohorts. The final cohort and outcome definitions provided a total of 84,070 patients and 880 outcomes (10.5%).

Results

As shown in Table 1, below, the ML model significantly outperformed the KFRE model in both predictive performance and patient population coverage. The ML model achieved a validated AUC of 0.94 over the 1-year prediction window, as compared to the validated AUC of 0.90 for the KFRE model. Moreover, the ML model achieved 100% patient coverage, as compared to the 6.5% patient coverage achieved by the KFRE model.

TABLE 1

ML Model and KFRE Model Predictive Performance

|  | ML Model | KFRE Model |
|---|---|---|
| Patient Coverage | 100% | 6.5% |
| AUC | 0.94 | 0.90 |
| Sensitivity at Top Quintile | 0.89 | 0.77 |
| Specificity at Top Quintile | 0.82 | 0.80 |

Table 1 also shows that the LASSO ML model achieved a higher sensitivity within the top quintile of riskiest patients (0.891) vs. the KFRE's sensitivity (0.77) that was only achievable on 6.5% of the patients.

Because renal decline trajectories vary among CKD patients, intensive monitoring, frequency of follow-up appointments, dialysis planning, transplant referral, and early creation of arteriovenous fistula should be reserved for those with highest progression risk. In improving recall performance of a risk score, more patients become eligible for risk stratification as compared to the KFRE model. The increased sensitivity and patient coverage of the ML models can result in a much more powerful tool for driving preemptive care.

A common complaint with respect to ML models is their poor interpretability due to algorithmic complexity. To mitigate this, the ML model was configured to automatically generate a human-readable feature list comprising important features and corresponding feature weights.

Table 2, below, shows a summary of the important features for predicting renal failure within a 1-year prediction window, as determined by the ML model. And Table 3, below, shows a detailed list of top predictive features with corresponding weights. It will be appreciated that renal failure codes include DP codes specifying CKD stage 5 and/or ESRD. And unspecified kidney failure codes include DP codes that are suggestive of acute renal failure or AKI, and that are not renal failure codes.

TABLE 2

Summary of ML Model Top Features

| Rank | Feature |
|---|---|
| 1 | eGFR (summary statistics) |
| 2 | Age |
| 3 | Total number of DP codes |
| 4 | BUN/Cr ratio (summary statistics) |
| 5 | Race |
| 6 | Total time patient had hypertensive CKD |
| 7 | Total time patient had liver cirrhosis |
| 8 | Total time patient had glomerular diseases |
| 9 | Total time patient had anemia |
| 10 | Total time patient had Elixhauser renal failure comorbidity |
| 11 | Total time patient had unspecified kidney failure code |
| 12 | Total time patient had polyneuropathy |
| 13 | Total time patient had encephalopathy |
| 14 | Total time patient had type I diabetes mellitus |
| 15 | Total time patient had hypertensive heart disease and CKD |

TABLE 3

Detailed List of ML Model Top Features

| Feature | Weight |
|---|---|
| Most recent eGFR | −0.204 |
| Minimum eGFR | −0.179 |
| Age | −0.167 |
| Total number of DP codes | −0.138 |
| Most recent BUN:Cr ratio | 0.138 |
| Minimum BUN:Cr ratio | −0.126 |
| Mean eGFR | −0.123 |
| Race | −0.119 |
| Mean BUN:Cr ratio | −0.114 |
| Total time patient had hypertension complicated | −0.114 |
| Total time patient had liver cirrhosis | −0.108 |
| Total time patient had glomerular diseases | −0.106 |
| Total time patient had anemia | −0.097 |
| Total time patient had unspecified renal failure | −0.095 |
| Total time patient had polyneuropathy | −0.095 |
| Total time patient had encephalopathy | −0.093 |
| Total time patient had type 1 diabetes mellitus | −0.093 |
| Total time patient had hypertensive heart disease and CKD | −0.092 |

Experiment 2

In Experiment 2, an ML system comprising a regularized logistic regression ML model was employed to identify patients who were at risk of requiring renal replacement therapy ("RRT") within 185 days (approximately six months). The experiment utilized patient data from an EHR system maintained by The Rogosin Institute.

An outcome (the "RRT-required" outcome) was defined to require one or more of the following events within 185 days: (1) a validated, sustained decline in GFR value to 10 ml/min/1.73 m$^2$; (2) a validated dialysis initiation event; or (3) a validated kidney transplant event. According to KDIGO, an eGFR value of 10 ml/min/1.73 m$^2$ represents an upper limit on when dialysis should be initiated. See "Summary of Recommendation Statements," Kidney International Supplements 3:1 (2013) pp. 5-14 (incorporated by reference herein in its entirety). And the 185-day predication window was considered sufficient time for a multidisciplinary care team at The Rogosin Institute to educate a patient of the risks of RRT, to prepare the patient for dialysis treatment by ensuring venous access was in place and/or to start preparing for a renal transplant.

Features were created, as discussed above, relating to each patient's demographics information, DP information (including comorbidities), lab tests information, and medications information. Model validation was performed on a patient cohort curated to include only patients associated with advanced kidney function loss—defined as a median eGFR value of less than 35 ml/min/1.73 m$^2$ over a 90 day period immediately preceding the prediction start date (0-90 days). The cohort and outcome definitions provided a total of 4,450 patients and 580 validated outcomes (13.0%).

Results

As shown in Table 4, below, the ML model achieved a validated AUC of 0.934. Within the 155 patient outcomes in the top risk quintile of the validation group, the ML model achieved a sensitivity of 0.832 and a specificity of 0.896.

TABLE 4

ML Model Performance

| Performance Metric | Value |
| --- | --- |
| AUC | 0.931 |
| Sensitivity at Top Quintile | 0.832 |
| Specificity at Top Quintile | 0.896 |

Table 5, below, shows a summary of important features for predicting the RRT-required outcome within 185 days, as determined by the regularized logistic regression model. And Table 6, below, shows a detailed list of top predictive features with corresponding weights.

TABLE 5

Summary of ML Model Top Features

| Rank | Feature |
| --- | --- |
| 1 | Serum Cr (summary statistics) |
| 2 | eGFR (summary statistics) |
| 3 | Bicarbonate (summary statistics) |
| 4 | Serum calcium (summary statistics) |
| 5 | BUN (summary statistics) |
| 6 | Phosphorous (summary statistics) |
| 7 | Urine protein (summary statistics) |
| 8 | Serum albumin (summary statistics) |

TABLE 6

Detailed List of ML Model Top Features

| Feature | Weight |
| --- | --- |
| Median eGFR (0-90 days) | −0.492 |
| Most recent eGFR | −0.470 |
| Median bicarbonate/Cr ratio (0-90 days) | −0.411 |
| Median calcium/Cr ratio (0-90 days) | −0.397 |
| Median albumin/Cr ratio (0-90 days) | −0.247 |
| Median BUN/bicarbonate ratio (0-90 days) | 0.244 |
| Median BUN/Cr ratio (0-90 days) | −0.226 |
| Median phosphorus/calcium ratio (0-90 days) | −0.208 |
| Median phosphorus/Cr ratio (0-90 days) | −0.207 |

As shown in the above tables, the ML model makes extensive use of summary statistics for various lab tests information. As discussed above, summary statistics may include various combinations, ratios and aggregations for a given variable (e.g., median, mean, minimum value, maximum value and standard deviation). The model also employs differences in aggregated values within time windows leading up to the prediction period (e.g., a 90-day period preceding the prediction window start date). As discussed above, eGFR values employed by the ML model were calculated using the CKD-EPI formula.

Experiment 3

In Experiment 3, random forest ML models were employed to predict risk of two renal function decline outcomes in diverse, clinically relevant patient cohort conditions in the continuum of CKD and ESRD. It was surprisingly found that the ML models were able to employ longitudinal patient data available in EHR systems to accurately identify patients at risk of renal function decline to CKD stage 3, where such patients did not have any previous kidney disease diagnoses.

Longitudinal input data was ingested from an EHR system maintained by the Veterans Affairs healthcare system. The input data included 1,780,262 patient records with an average history length of 6.86 years, and none of the patients was associated with initial CKD at the time of ingest.

The population was first analyzed to predict patients who would experience a decline in renal function from no kidney disease to at least CKD3a, over a 1-, 2- and 5 year period. Patients were determined to have no kidney disease according to the following requirements: (1) an eGFR greater than or equal to 90 ml/min/1.73 m$^2$, and (2) no presence of a DP code for CKD. And the outcome (the "incident CKD" outcome) was defined to require: (1) CKD3a or above, and (2) a validated eGFR value of less than 60 ml/min/1.73 m$^2$.

The population was then analyzed to determine which patients would continue to decline from having a baseline eGFR greater than or equal to 60 ml/min/1.73 m$^2$ to CKD3b over a 1-, 2- and 5-year period. The outcome (the "advanced CKD" outcome) was defined to require: (1) CKD3b or above, and (2) a validated eGFR value of less than 45 ml/min/1.73 m$^2$.

Features were created, as discussed above, relating to each patient's demographics information, DP information (including comorbidities), lab tests information, and medications information. In order to generate temporally normalized data representations, the lab tests information provided to the ML system comprised various summary statistics (e.g., minimum, maximum, mean, and/or standard deviation) over multiple time periods (e.g., over 30-, 90-, 180-day, and/or 365-day periods preceding the prediction window start date, and/or over the entire observation window).

The features were provided to the ML system to determine risk information for each patient according to the incident CKD and advanced CKD outcomes over 1-, 2- and 5-year prediction windows.

Results

As shown in Table 7, below, the ML models were able to achieve high AUCs while using longitudinal data that is commonly available in EHR systems. For example, the one-year incident CDK model had an AUC of 0.839 and the one-year advanced CKD model had an AUC of 0.871.

TABLE 7

Performance of Incident CKD Model and Advanced CKD Model

|  | Performance Metric | One Year | Two Years | Five Years |
|---|---|---|---|---|
| Incident CKD Model | AUC | 0.839 | 0.808 | 0.791 |
|  | Outcome (%) | 0.282% | 0.572% | 2.034% |
|  | Sensitivity at Top Quartile | 0.754 | 0.723 | 0.651 |
|  | Specificity at Top Quartile | 0.751 | 0.753 | 0.758 |
| Advanced CKD Model | AUC | 0.871 | 0.853 | 0.830 |
|  | Outcome (%) | 0.191% | 0.474% | 2.018% |
|  | Sensitivity at Top Quartile | 0.825 | 0.784 | 0.739 |
|  | Specificity at top Quartile | 0.751 | 0.753 | 0.760 |

It was surprisingly found that the ML models offer strong predictive value in identifying both patients at risk for incidence of new CKD and patients at risk of progressing from no CKD or mild CKD to CKD3b via the use of longitudinal patient data that is typically available in EHR systems. Although the primary focus in kidney disease care has been to prevent CKD progression to ESRD, early identification of patients at risk of new CKD may actually provide larger public health and population health benefits. For example, the ML models discussed in this example can be leveraged to encourage early, proactive engagement with older patients having high Charlson Comorbidity Index scores—even when such patients have no prior history of CKD.

Tables 8-10, below, shows a summary of important features determined by the ML models for the incident CKD outcome over 1-, 2- and 5-year prediction windows. It will be appreciated that a "kidney disease code" includes DP codes specifying CKD, glomerulopathy, congenital kidney disease and other kidney abnormalities.

TABLE 8

Summary of ML Model Top Features for Predicting Incident CKD Within 1 Year

| Rank | Feature |
|---|---|
| 1 | BUN/Cr ratio (summary statistics) |
| 2 | BUN (summary statistics) |
| 3 | Presence of kidney disease code |
| 4 | Age |
| 5 | eGFR (summary statistics) |
| 6 | Patient prescribed diuretics (ATC class C03) |
| 7 | Patient prescribed anti-hypertensive medication |
| 8 | Charlson Comorbidity Index score |
| 9 | Patient prescribed calcium channel blockers (ATC class C08) |
| 10 | Serum potassium (summary statistics) |

TABLE 9

Summary of ML Model Top Features for Predicting Incident CKD Within 2 Years

| Rank | Feature |
|---|---|
| 1 | BUN (summary statistics) |
| 2 | BUN/Cr ratio (summary statistics) |
| 3 | Presence of kidney disease code |
| 4 | Age |
| 5 | Most recent eGFR value |
| 6 | Charlson Comorbidity Index score |

TABLE 9-continued

Summary of ML Model Top Features for Predicting Incident CKD Within 2 Years

| Rank | Feature |
|---|---|
| 7 | eGFR (summary statistics) |
| 8 | Patient prescribed diuretics (ATC class C03) |
| 9 | Patient prescribed anti-hypertensive medication |
| 10 | Serum albumin (summary statistics) |

TABLE 10

Summary of ML Model Top Features for Predicting Incident CKD Within 5 Years

| Rank | Feature |
|---|---|
| 1 | Charlson Comorbidity Index score |
| 2 | Age |
| 3 | Presence of diabetes mellitus code |
| 4 | Patient prescribed diabetes medication (ATC class A10) |
| 5 | Patient prescribed non-insulin diabetic medication |
| 6 | Presence of kidney disease code |
| 7 | BUN (summary statistics) |
| 8 | BUN/Cr ratio (summary statistics) |
| 9 | Serum albumin (summary statistics) |
| 10 | Blood pressure (summary statistics) |

Interestingly, it was found that, as the ML model predicts on the incident CKD outcome across longer prediction windows, features based on lab values became less predictive and features based on comorbidities became more predictive. It will be appreciated that, unlike the KFRE and other static models, the ML models automatically determine important features and their corresponding weights. In this experiment, the ML model appeared to shift consideration from more transient measures (e.g., contemporaneous lab predictors) to long-range predictors (e.g., chronic comorbid conditions) as the length of the prediction window increased.

Experiment 4

In Experiment 4, an ML system was shown to be able to integrate non-standard patient information, including novel biomarkers information, with data typically found in EHR systems to increase prediction performance for multiple outcomes. The ML system was found to successfully bin patients according to calculated risk scores and to provide conservative cost of care estimates for such patients based on incomplete payer data.

Input data was ingested from a healthcare system associated with the Icahn School of Medicine at Mount Sinai comprising two clinically distinct patient cohorts. A first patient dataset included 871 patients having a diagnosis of type 2 diabetes. And a second patient dataset included 497 patients having verified risk-variant alleles in the APOL1 (i.e., two copies of the APOL1 renal risk variants: G1/G1, G2/G2, or G1/G2). In addition to the EHR data used in Experiments 1-3, the input data associated with both patient cohorts included measurements relating to TNFR1, TNFR2, and KIM1 biomarkers for each of the patients. The first patient dataset also included measurements relating to endostatin biomarkers for each of the patients.

A "diabetes cohort" was curated from the first patient dataset to include only patients associated with at least one data record and at least one eGFR within a 5-year period preceding an enrollment start date. The resulting diabetes cohort included 420 patients, with 100 of such patients (24%) experiencing a validated 40% decline in eGFR from eGFR baseline within a 5-year prediction window. Any eGFR measurements determined to have been taken during an AKI episode were not considered to satisfy the 40% eGFR decline criterion.

An "APOL1 cohort" was curated from the second patient dataset to include only patients associated with at least one data record and at least one eGFR within a 3-year period preceding the enrollment start date. The resulting APOL1 cohort included 411 patients, with 20 of such patients (5%) experiencing a validated 40% decline in eGFR from eGFR baseline within a 3-year prediction window. Again, any eGFR measurements determined to have been taken during an AKI episode were not considered to satisfy the 40% eGFR decline criterion.

For the purposes of quantifying incremental predictive performance added by the supplemental biomarkers information, three models were created and evaluated concurrently. A "Baseline Model" was created to include features relating to age, sex, race, baseline eGFR strata (eGFR less than 60 ml/min/1.73 m$^2$ or at least 60 ml/min/1.73 m$^2$), albuminuria strata (albumin-to-creatinine ratio less than or equal to 1,000 or greater than 1,000 mg/g Cr), systolic and diastolic blood pressure, and whether patients were on blood pressure medications. A "Biomarkers Model" was created to use only normalized values for TNFR1, TNFR2, KIM1, and endostatin as features. And, an "Integrated Model" was created to employ features relating to all relevant patient information in the input data, as well as the biomarkers information used by the Biomarker Model.

Due to the small population size in both data sets, logistic regression and RF were evaluated with feature cross-validation (Monte Carlo-style) methods to ensure robustness. The models were each run 100 times and the average AUC was determined. Representative example models were selected in order to report out the performance metrics and the important features list.

Results

With respect to the diabetes cohort, the AUCs for the Baseline Model, Biomarkers Model, and Integrated Model were 0.715, 0.807, and 0.878, respectively. The Integrated Model also achieved a sensitivity of 0.667, and a specificity of 0.938 at the top risk quintile.

And, with respect to the APOL1 cohort, the AUCs for the Baseline Model, Biomarkers Model, and Integrated Model were 0.727, 0.80, and 0.855, respectively. The Integrated Model also achieved a sensitivity of 0.677, and a specificity of 0.822 at the top risk quintile.

The Integrated Model was also found to allow for stratification of patients at risk for 40% eGFR decline. Specifically, this model was able to determine risk scores for each patient and categorize the patients into "high risk," "medium risk," and "low risk," categories according to such risk scores. Table 11, below, shows the mean eGFR change within the risk groups.

TABLE 11

Mean eGFR Change Over Time for Risk Groups

|  | Diabetes Cohort (N = 411) (eGFR change at 5 years) | APOL1 Cohort (N = 420) (eGFR change at 3 years) |
| --- | --- | --- |
| High Risk | −58% from index eGFR (n = 14) | −55% from index eGFR (n = 76) |
| Medium Risk | −11% from index eGFR (n = 58) | −14% from index eGFR (n = 180) |
| Low Risk | +1% from index eGFR (n = 339) | −2% from index eGFR (n = 164) |

The method of binning patient by risk scores was found to allow for effective stratification of cumulative costs of services incurred over time. For example, in a retrospective review for the diabetes cohort over a 5-year period, the high-risk patient group averaged $214,873 in cumulative costs per patient, the medium-risk group averaged $88,993 in cumulative costs per patient, and the low-risk group averaged $44,267 in cumulative costs per patient. As another example, over a 3-year period, the high-risk group averaged $138,288 in cumulative costs per patient, the medium-risk group averaged $60,987 in cumulative costs per patient, and the low-risk group averaged $30,167 in cumulative costs per patient.

It will be appreciated that the above amounts comprise lower-bound, conservative estimates, as complete payer data was not available. Each hospitalization was estimated to be $30,000 per admission. The cumulative results obtained were consistent with studies showing annual costs of about $46,000 for CKD stage 5 patients, which extrapolates to $230,000 over five years.

The Integrated ML models employed in Experiment 4 were configured to automatically generate a feature list comprising predictive features and corresponding feature weights. Tables 12 and 13, below, show summaries of predictive features determined by the Integrated ML models for the diabetes cohort and APOL1 cohort, respectively. And Table 14, below, shows a detailed list of such features with corresponding weights for the APOL1 cohort.

TABLE 12

Summary of Integrated ML Model Top Features for Predicting Renal Failure Outcome in Diabetes Cohort

| Rank | Feature |
| --- | --- |
| 1 | KIM 1 biomarker |
| 2 | Serum albumin (summary statistics) |
| 3 | TNFR1 biomarker |
| 4 | Endostatin biomarker |
| 5 | UACR (summary statistics) |
| 6 | Urine microalbumin (summary statistics) |
| 7 | eGFR (summary statistics) |
| 8 | Serum calcium (summary statistics) |
| 9 | TNFR2 biomarker |
| 10 | Hemoglobin (summary statistics) |

TABLE 13

Summary of Integrated ML Model Top Features for Predicting Renal Failure Outcome in APOL1 Cohort

| Rank | Feature |
| --- | --- |
| 1 | TNFR2 biomarker |
| 2 | eGFR (summary statistics) |
| 3 | KIM1 biomarker |
| 4 | Serum albumin (summary statistics) |
| 5 | TNFR1 biomarker |
| 6 | Hemoglobin (summary statistics) |
| 7 | Total number of hypertension DP codes |
| 8 | Total number of CHF DP codes |
| 9 | Total number of IHD DP codes |
| 10 | Serum calcium (summary statistics) |

TABLE 14

Detailed List of Integrated ML Model Top Features for Predicting Renal Failure Outcome in APOL1 Cohort

| Feature* | Weight |
| --- | --- |
| TNFR2 biomarker value | 0.03983 |
| Total number of eGFR measurements (0-365 days) | 0.03464 |
| Standard deviation of eGFR values | 0.02883 |
| KIM1 biomarker value | 0.02820 |
| Mean albumin | 0.02780 |
| Total number of eGFR measurements | 0.02669 |
| Mean albumin (0-365 days) | 0.02315 |
| TNFR1 biomarker value | 0.02136 |
| Mean hemoglobin (0-365 days) | 0.01871 |
| Minimum eGFR (0-365 days) | 0.01815 |
| Total number of hypertension complicated DP codes | 0.01752 |
| Mean hemoglobin | 0.01646 |
| Total number of CHF DP codes | 0.01630 |
| Standard deviation of eGFR (0-365 days) | 0.01554 |
| Minimum eGFR | 0.01547 |
| Most recent eGFR | 0.01453 |
| Total number of IHD DP codes | 0.01401 |
| Maximum eGFR (0-365 days) | 0.01386 |
| Mean eGFR (0-365 days) | 0.01374 |
| Mean calcium | 0.01357 |
| Mean UPCR | 0.01325 |
| Total number of hypertension uncomplicated | 0.01312 |
| Mean bicarbonate | 0.01184 |
| Mean eGFR | 0.01142 |
| Total time patient had CHF, upper half | 0.01126 |
| Total number of CKD DP codes | 0.01108 |
| Mean UPCR (0-365 days) | 0.01103 |
| Mean calcium (0-365 days) | 0.01099 |
| Mean hemoglobin A1C | 0.01072 |
| Total time patient had heart attack, lower half | 0.01038 |
| Total number of diabetes mellitus complicated DP codes | 0.01030 |
| Mean hemoglobin A1C (0-365 days) | 0.01024 |
| Maximum eGFR | 0.01014 |
| Total time patient had heart attack, upper half | 0.01013 |
| Total time patient had CHF, lower half | 0.01008 |
| Mean bicarbonate (0-365 days) | 0.00973 |
| Total time patient had cardiac arrhythmia, lower half | 0.00972 |
| Total time patient had hypertension uncomplicated, lower half | 0.00917 |
| Mean phosphorus | 0.00898 |
| Total time patient had cardiac arrhythmia, upper half | 0.00897 |
| Total time patient had hypertension complicated, lower half | 0.00886 |
| Total number of hyperlipidemia negative DP codes | 0.00885 |
| Presence of hypertension complicated comorbidity diagnosis | 0.00869 |
| Total time patient had renal failure, upper half | 0.00860 |
| Total time patient had hypertension uncomplicated, upper half | 0.00820 |
| Total number of Hepatitis C DP codes | 0.00811 |
| Total number of fatigue and weakness DP codes | 0.00778 |
| Total number of diabetes mellitus type 2 DP codes | 0.00728 |
| Total time patient had Renal Failure, lower half | 0.00721 |

It will be appreciated that the above lists of predictive features determined by the Integrated ML model include features relating to blood levels of TNFR1, TNFR2, and KIM1 (and optionally endostatin) biomarkers, along with several features relating to lab tests and comorbidities. Accordingly, this experiment shows that these biomarkers have independent value in predicting renal failure (whether to 40% eGFR decline or ESRD).

Moreover, this experiment show that, in patients with diabetes mellitus type 2 and preserved eGFR and in patients with high-risk APOL1 genetic variants, the use of features relating to biomarker data and various longitudinal EHR data in combination with advanced ML techniques provides superior results for discrimination and prediction of kidney outcomes. These approaches can be applied in routine clinical care for early risk stratification, which may ultimately lead to better clinical outcomes.

Various embodiments are described in this specification, with reference to the detailed discussed above, the accompanying drawings, and the claims. Numerous specific details are described to provide a thorough understanding of various embodiments. However, in certain instances, well-known or conventional details are not described in order to provide a concise discussion. The figures are not necessarily to scale, and some features may be exaggerated or minimized to show details of particular components. Therefore, specific structural and functional details disclosed herein are not to be interpreted as limiting, but merely as a basis for the claims and as a representative basis for teaching one skilled in the art to variously employ the embodiments.

The embodiments described and claimed herein and drawings are illustrative and are not to be construed as limiting the embodiments. The subject matter of this specification is not to be limited in scope by the specific examples, as these examples are intended as illustrations of several aspects of the embodiments. Any equivalent examples are intended to be within the scope of the specification. Indeed, various modifications of the disclosed embodiments in addition to those shown and described herein will become apparent to those skilled in the art, and such modifications are also intended to fall within the scope of the appended claims.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

All references, including patents, patent applications and publications cited herein are incorporated herein by reference in their entirety and for all purposes to the same extent as if each individual publication or patent or patent application was specifically and individually indicated to be incorporated by reference in its entirety for all purposes.

What is claimed is:

1. A method of determining and automatically updating a risk of renal function decline for a plurality of patients via a machine-learning system, the method comprising:
   A. storing, in a memory of a computer, a plurality of patient records configured to be analyzed by a trained machine-learning system in communication with the computer via a network, each of the patient records storing patient information corresponding to a unique patient from a plurality of patients, the patient information comprising:
      a plurality of demographics associated with the patient comprising:
         a demographic relating to an age of the patient; and
         a demographic relating to a gender of the patient;
      a plurality of lab tests associated with the patient, each lab test of the plurality of lab tests associated with lab test information comprising a date, a variable and a value relating to the variable, the plurality of lab tests comprising:
         a first set of lab tests, each associated with a biomarker variable relating to one of:
            tumor necrosis factor receptor-1 ("TNFR1"), tumor necrosis factor receptor-2 ("TNFR2"), and kidney injury molecule-1 ("KIM1");
         a second set of lab tests comprising:
            a first lab test associated with a first date and a first lab test variable; and
            a second lab test associated with a second date that is different than the first date and a second lab test variable that is different than the first lab test variable,
         wherein each lab test of the second set of lab tests is associated with a lab test variable relating to at least one of: estimated glomerular filtration rate ("eGFR"), urine albumin-creatinine-ratio ("UACR"), serum creatinine, blood urea nitrogen ("BUN"), serum sodium, serum potassium, serum chloride, serum bicarbonate, serum calcium, serum albumin, urine creatinine, urine albumin, urine microalbumin, urine protein, complete blood count ("CBC") panel, liver function panel, lipid profile panel, a coagulation panel, magnesium, phosphorus, brain natriuretic peptide ("BNP"), hemoglobin A1 c ("HbA1c"), uric acid and endostatin;
   B. transmitting, by the computer, to the trained machine-learning system, the patient records, wherein the trained machine-learning system has previously been trained with training data such that the system has identified important features from a plurality of potential features and has calculated and stored weights associated with such important features based on an importance of the respective feature in determining a probability that a patient will experience an outcome relating to a decline in renal function within a prediction time period, the important features comprising:
      a plurality of demographic features, each relating to at least one demographic of
      the plurality of demographics; and
      a plurality of lab test features, each relating to at least one lab test of the plurality of lab tests, the plurality of lab test features comprising a feature relating to the first lab test variable, the second lab test variable, and a time period that includes both the first date and the second date;
      wherein the trained machine-learning system is configured to calculate, for each of the transmitted patient records, a feature value for each of the important features based on the patient information associated with the respective patient record and the stored weight associated with the respective important feature, and
      wherein the trained machine-learning system is configured to determine, for each of the transmitted patient records, a current risk score based on the feature values calculated for the respective patient record, the current risk score relating to the probability that the respective patient will experience the outcome within the prediction time period;
   C. receiving, by the computer, from the trained machine-learning system, the current risk scores;
   D. storing, by the computer, the current risk scores in the memory, each current risk score associated with the patient record to which it corresponds;
   E. determining, by the computer, whether the current risk score associated with each of the patient records is greater than a predetermined threshold and, if so, transmitting a notification comprising at least a portion of the respective patient record to one or more providers associated with the respective patient; and
   F. continuously determining, by the computer, for each of a plurality of data sources in communication with the computer via the network, the plurality of data sources comprising an electronic health records ("EHR") system, whether new patient information is available and, if so:
  automatically ingesting, by the computer, the new patient information;
preprocessing, by the computer, the new patient information in accordance with a centralized data schema to create preprocessed data records;
correlating, by the computer, each of the preprocessed data records to one of the patient records stored in the memory to update the patient records with the correlated preprocessed data records; and
repeating steps B-E for the updated patient records to thereby determine current risk scores and transmit notifications to providers when such current risk scores are greater than the predetermined threshold.

2. A method according to claim 1, wherein the plurality of demographics further comprises a demographic relating to a race of the patient.

3. A method according to claim 1, wherein the first set of lab tests comprises:
  a lab test associated with TNFR1;
  a lab test associated with TNFR2; and
  a lab test associated with KIM1.

4. A method according to claim 1, wherein the lab test variable associated with each of the second set of lab tests relates to at least one of: eGFR, serum creatinine, BUN, serum bicarbonate, serum phosphorus, serum calcium, urine creatinine, urine albumin, urine microalbumin, urine protein, and UACR.

5. A method according to claim 1, wherein the lab test information further comprises one or more of: a lab test identifier, a unit relating to the lab test value, a reference range of values, a sample type, facility identification information, provider information, radiological imaging data, and clinical notes.

6. A method according to claim 1, wherein:
  the patient information further comprises one or more diagnoses associated with the patient, each diagnosis of the one or more diagnoses associated with diagnosis information comprising a diagnosis identifier; and
  the plurality of features further comprises a plurality of diagnosis features, each diagnosis feature of the plurality of diagnosis features relating to at least one diagnosis of the one or more diagnoses.

7. A method according to claim 6, wherein the one or more diagnoses comprises a first diagnosis associated with a kidney issue or a comorbidity.

8. A method according to claim 7, wherein:
  the first diagnosis is associated with the kidney issue; and
  the kidney issue relates to one of the group consisting of: polycystic kidney disease, renal agenesis, Alport Syndrome, rapidly progressive glomerulonephritis, focal segmental glomerulosclerosis, IgA nephropathy, membranous nephropathy, membranoproliferative glomerulopathy, mesangial proliferative glomerulopathy, minimal change disease, nephritic syndrome, nephrotic syndrome, nephrolithiasis, hypertensive nephropathy, analgesic nephropathy, diabetic nephropathy, lithium nephropathy, renal artery stenosis, Lupus nephritis, kidney myeloma, kidney amyloidosis, anti-glomerular basement membrane disease, fatigue or weakness, edema, and proteinuria.

9. A method according to claim 7, wherein
the first diagnosis is associated with the comorbidity; and
the comorbidity relates to one of the group consisting of:
  alcohol abuse, anemia deficiency, rheumatoid arthritis, blood loss anemia, cardiac arrhythmia, congestive heart failure ("CHF"), chronic obstructive pulmonary disease ("COPD"), coagulopathy, acquired immunodeficiency syndrome ("AIDS") or human immunodeficiency virus ("HIV"), depression, diabetes, drug abuse, hypertension, hypothyroidism, liver disease, lymphoma, a fluid or electrolyte disorder, metastatic cancer, a neurological disorder, obesity, paralysis, peripheral vascular disease, psychosis, and pulmonary circulation disorder.

10. A method according to claim 9, wherein the plurality of diagnosis features further comprises a feature relating to a Charlson Comorbidity Index ("CCI") score calculated for the first diagnosis.

11. A method according to claim 6, wherein the diagnosis information further comprises one or more of: a diagnosis date, provider information, equipment information, clinical notes and vital signs information.

12. A method according to claim 1, wherein:
  the patient information further comprises one or more medications associated with the patient, each medication of the one or more medications associated with medication information comprising a medication identifier; and
  the plurality of features further comprises a plurality of medication features, each medication feature of the plurality of medication features relating to at least one medication of the one or more medications.

13. A method according to claim 12, wherein the medication information further comprises at least one of the group consisting of: a medication date, a medication type, a concentration, a quantity, an amount, date information, refill information, provider information, and clinical notes.

14. A method according to claim 13, wherein the one or more medications comprises one or more of the group consisting of: an antibiotic medication; a non-steroidal anti-inflammatory drug ("NSAID") medication; a beta-adrenergic receptor blocker medication; a dihydropyridine medication; an angiotensin II receptor blocker ("ARB") medication; an angiotensin-converting enzyme ("ACE") inhibitor medication; a sodium-glucose Cotransporter-2 (SGLT2) inhibitor medication; a Thiazide-class diuretic medication; a Loop-diuretic medication; and a HMG-CoA reductase inhibitor medication.

15. A method according to claim 1, wherein the patient information comprises genetic information indicating that one or more risk variant alleles in an Apolipoprotein L1 gene ("APOL1") of the patient are expressed.

16. A method according to claim 15, wherein the plurality of features further comprises one or more features relating to the genetic information.

17. A method according to claim 1, further comprising:
  determining that the current risk score associated with one of the patient records satisfies a workflow rule associated with a patient workflow; and
  executing the patient workflow.

18. A method according to claim 17, wherein said executing the patient workflow comprises:
  determining a treatment recommendation for the patient, based on the current risk score,
  wherein the notification further comprises the treatment recommendation.

19. A method according to claim 1, wherein the plurality of data sources further comprises at least one of the group consisting of: a health facility system, an insurance system, a payment system, a user device, a medical device, a biometric device, and an engagement system.

* * * * *